(12) United States Patent
Wang et al.

(10) Patent No.: US 9,713,623 B2
(45) Date of Patent: Jul. 25, 2017

(54) TRIAZINE CATIONIC POLYMERS AND METHODS OF USE THEREOF

(71) Applicant: The Charlotte Mecklenburg Hospital Authority, Charlotte, NC (US)

(72) Inventors: Mingxing Wang, Matthews, NC (US); Qi Lu, Charlotte, NC (US)

(73) Assignee: The Charlotte-Mecklenburg Hospital Authority, Charlotte, NC (US)

( * ) Notice: Subject to any disclaimer, the term of this patent is extended or adjusted under 35 U.S.C. 154(b) by 0 days.

(21) Appl. No.: 14/674,491

(22) Filed: Mar. 31, 2015

(65) Prior Publication Data
US 2015/0273073 A1    Oct. 1, 2015

Related U.S. Application Data

(60) Provisional application No. 61/972,858, filed on Mar. 31, 2014.

(51) Int. Cl.
| | | |
|---|---|---|
| *C07D 251/40* | (2006.01) | |
| *A61K 31/53* | (2006.01) | |
| *A61K 31/713* | (2006.01) | |
| *A61K 47/48* | (2006.01) | |
| *A61K 31/69* | (2006.01) | |
| *C12N 15/113* | (2010.01) | |
| *C12N 15/11* | (2006.01) | |
| *A61K 31/7105* | (2006.01) | |
| *A61K 31/711* | (2006.01) | |
| *C08G 79/025* | (2016.01) | |
| *C08G 81/00* | (2006.01) | |
| *C08G 69/10* | (2006.01) | |
| *C08G 73/02* | (2006.01) | |
| *C08G 73/06* | (2006.01) | |

(52) U.S. Cl.
CPC .......... *A61K 31/69* (2013.01); *A61K 31/711* (2013.01); *A61K 31/713* (2013.01); *A61K 31/7105* (2013.01); *A61K 47/48192* (2013.01); *A61K 47/48215* (2013.01); *C08G 69/10* (2013.01); *C08G 73/0206* (2013.01); *C08G 73/0644* (2013.01); *C08G 79/025* (2013.01); *C08G 81/00* (2013.01); *C12N 15/111* (2013.01); *C12N 15/113* (2013.01); *C12N 2310/11* (2013.01); *C12N 2310/3233* (2013.01); *C12N 2320/33* (2013.01)

(58) Field of Classification Search
CPC ...... A61K 31/69; A61K 31/713; A61K 38/02; A61K 47/48061
USPC ........................................................ 544/194
See application file for complete search history.

(56) References Cited

U.S. PATENT DOCUMENTS

| | | | | | |
|---|---|---|---|---|---|
| 3,301,797 | A | * | 1/1967 | Drucker ............. | C08G 73/0644 526/258 |
| 4,115,540 | A | | 9/1978 | Digenis et al. | |
| 4,400,505 | A | * | 8/1983 | Loffelman ............. | C08F 220/34 524/100 |
| 4,879,341 | A | | 11/1989 | Tsumiyama et al. | |
| 5,652,327 | A | * | 7/1997 | Kang ................... | C08G 65/4006 526/258 |
| 2002/0182172 | A1 | * | 12/2002 | Bentley ............. | A61K 47/48215 424/78.36 |

FOREIGN PATENT DOCUMENTS

| | | |
|---|---|---|
| CA | 2789068 A1 | 9/2011 |
| WO | WO 2008/079973 A2 | 7/2008 |

OTHER PUBLICATIONS

Cao et al. "Design of Poly(vinyldiaminotriazine)-Based Nonviral Vectors via Specific Hydrogen Bonding with Nucleic Acid Base Pairs", Adv. Funct. Mater. 17:246-252 (2007).
Notification of Transmittal of the International Search Report and the Written Opinion of the International Searching Authority, or the Declaration corresponding to International Application No. PCT/IP15/52373 mailed Jul. 27, 2015.
Notification Comcerning Transmittal of International Preliminary Report of Patentability corresponding to International Application No. PCT/IB2015/052373 mailed Oct. 13, 2016.

* cited by examiner

*Primary Examiner* — Venkataraman Balasubramanian
(74) *Attorney, Agent, or Firm* — Myers Bigel, P.A.

(57) ABSTRACT

The present invention provides compounds of Formula I or Formula II:

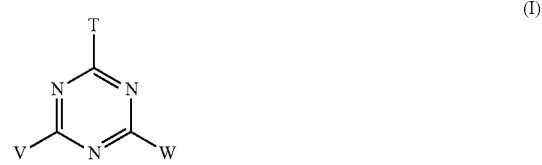

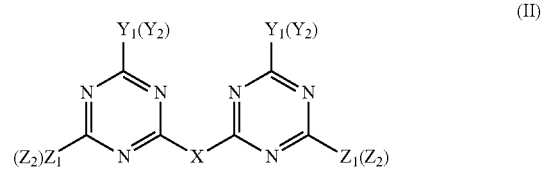

wherein:
T, V, W, Y and Z are each independently selected from the group of substituents described herein, and X is a linker as further described herein. The present invention further provides compositions and conjugates including the compounds as well as methods of using these compounds including, but not limited to, methods of preventing, treating and/or diagnosing genetic disorders, such as muscular dystrophy, or non-genetic disorders as described herein.

10 Claims, 12 Drawing Sheets

1A₄1B₁,(10-5 μg)  1A₄1B₂,(10-5 μg)  1A₄1B₃,(10-5 μg)

TRIAZINE CATIONIC POLYMERS AND METHODS OF USE THEREOF

STATEMENT OF PRIORITY

This application claims priority to U.S. Provisional Application Ser. No. 61/972,858, filed Mar. 31, 2014, the disclosure of which is incorporated by reference in its entirety.

RESERVATION OF COPYRIGHT

A portion of the disclosure of this patent document contains material which is subject to copyright protection. The copyright owner, The Charlotte-Mecklenburg Hospital Authority, doing business as "Carolinas HealthCare System," Charlotte, N.C., has no objection to the reproduction by anyone of the patent document or the patent disclosure, as it appears in the U.S. Patent and Trademark Office patent file or records, but otherwise reserves all copyright rights whatsoever.

FIELD OF THE INVENTION

The present invention relates to triazine cationic polymers as well as their use in transporting therapeutic agents or diagnostic agents into cells and methods of treating diseases.

BACKGROUND OF THE INVENTION

Over the past two decades, various polymer-based non-viral vectors for gene delivery have been developed by structure design and formulation. Most of the non-viral vectors currently developed are polycations. Among the polycations investigated, high molecular weight polyethylenimine (HPEI) has demonstrated a higher gene transfection efficiency in various types of cells both in vitro and in vivo. This attribute has contributed to its use to condense plasmid DNA effectively into colloidal particles via its proton-sponge effect. However, its non-degradability, aggregation, cytotoxicity and/or short-circulation time in vivo have limited its clinical applications. Modifications of HPEI to reduce cytotoxicity, while retaining its high potential to bind and condense plasmid DNA for gene delivery have been investigated previously, but with limited success. One effort has been to modify HPEI (25 k) with hydrophilic polyethylene glycol (PEG) aiming to primarily shield the surface charges of the PEI, thus reducing toxicity. However, this modification led to reduced transfection activity when compared to HPEI alone. Williams et al. synthesized a PEG550-PEI 2000 copolymer and examined the efficiency of the polymer for the delivery of 2'-O-methyl-phosphorothioate antisense oligonucleotide (2'-OMePS) in tibialis anterior (TA) muscle of mdx mice for Exon 23 skipping, but the efficiency was still limited and probably due to its hydrophilicity. Amphiphilies pluronic (such as F127, SP1017) have been evaluated and found effective in enhancing gene transfection efficiency of naked DNA or antisense oligonucleotides in skeletal muscle (Lu, Q L, Bou-Gharios, G and Partridge, T A. (2003). Non-viral gene delivery in skeletal muscle: a protein factory. *Gene Ther* 2003, 10, 131-142; Lemieux, P, Guerin, N, Paradis, G, Proulx, R, Chistyakova, L, Kabanov, A et al. (2000). A combination of poloxamers increases gene expression of plasmid DNA in skeletal muscle. *Gene Ther* 2000, 7, 986-991; Pitard, B, Pollard, H, Agbulut, O, Lambert, O, Vilquin, J T, Cherel, Y et al. (2002). A nonionic amphiphile agent promotes gene delivery in vivo to skeletal and cardiac muscles. *Hum Gene Ther* 2002, 13, 1767-1775; Cho, K C, Choi, S H and Park, T G. (2006). Low molecular weight PEI conjugated pluronic copolymer: Useful additive for enhancing gene transfection efficiency. *Macromol Res.* 2006, 14, 348-353).

Applicants have developed cationic amphiphilic polymers constructed from poloxamers/pluronic and polyamines and achieved considerable enhancement for plasmid DNA (pDNA) or antisense oligonucleotides (AOs) delivery in vitro and in vivo (Wang M X, Lu P J, Wu B, Tucker J D, Cloer C and Lu Q L. High efficiency and low toxicity of polyethyleneimine modified pluronics (PEI-Pluronic) as gene delivery carriers in cell culture and dystrophic mdx mice. *J Mater Chem* 2012; 22: 6038-6046; Wang M X, Wu B, Lu P J, Tucker J D, Cloer C and Lu Q L. Polyethylenimine Modified Pluronics (PCMs) Improve Morpholino Oligomers Delivery in Cell Culture and Dystrophic mdx Mice. *Mol Ther* 2013; 21: 210-216; Wang M X, Wu B, Tucker J D, Lu P J, Cloer C and Lu Q L. "Evaluation of Tris[2-(acryloyloxy) ethyl]isocyanurate Cross-linked Polyethylenimine as Antisense Morpholino Oligomer Delivery Vehicle in Cell Culture and Dystrophic mdx Mice". *Human Gene Therapy*, 2014, 25(5), 419-427; Wang M X, Tucker J D, Lu P J, Wu B, Lu Q L. "Tris[2-(acryloyloxy)ethyl]isocyanurate cross-linked low-molecular-weight polyethylenimine as gene delivery carriers in cell culture and dystrophic mdx mice", *Bioconjugate Chemistry*, 2012, 23, 837-845).

However, it is generally difficult to control the molecular size and composition of the polymers as well as the corresponding polymer-AO conjugates. This often results in poor reproducibility of copolymers and makes further optimization more difficult.

The success of gene/oligonucleotide therapies often relies on the ability of systems to deliver the therapeutic gene/oligonucleotides to the target tissue relatively efficiently and safely. Non-viral gene delivery systems, based on naked DNA/oligonucleotides, have advantages over viral vectors for simplicity of use and lack of specific immune response related to viral infection. However, naked DNA/oligonucleotides are generally difficult to deliver into target cells in vivo. An ideal non-viral gene carrier typically must condense DNA/oligonucleotides into small polyplexes, protect them from enzymatic degradation, penetrate cell membranes, and deliver their cargo into the nucleus efficiently without causing significant cytotoxicity. Consequently, a number of approaches have been proposed to develop cationic polymers with higher gene transfection efficiency and lower cytotoxicity. However, development and use of relatively effective and safe vectors for plasmid DNA (pDNA)/oligonucleotide delivery generally remain challenging, especially for treating muscle and other genetic disorders, which require systemic delivery.

SUMMARY OF THE CLAIMED INVENTION

Provided herein according to some embodiments of the present invention are compounds of Formulas I and II:

(I)

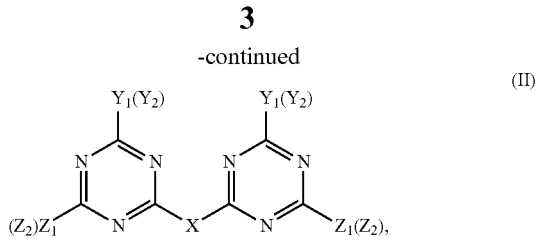

(II)

wherein embodiments may contain at least one amphiphilic substitute, and at least one cationic substitute, and further with or without therapeutic/diagnostic agents.

The present invention further provides a series of triazine-cored amphiphilic cationic polymers as well as conjugates of the same.

Also provided are pharmaceutical compositions including compounds of Formula I or Formula II, a therapeutic agent, and optionally a pharmaceutically acceptable carrier. In some embodiments, the composition is formulated for intravenous, oral, subcutaneous, intradermal, intramucosal, intranasal, topical or intramuscular administration.

Further provided are methods of preventing or treating a genetic disease or non-genetic disease in a subject, comprising administering to the subject an effective amount of a compound of Formula I or Formula II complexed with a therapeutic or diagnostic agent and/or a suitable carrier. In some embodiments, the genetic disease is muscular dystrophy.

Still further provided are uses of compounds of Formula I or Formula II, a therapeutic or diagnostic agent and/pr a suitable carrier in a method of therapeutic treatment or diagnosis. In some embodiments, the compounds are used to treat a genetic disease. In still further embodiments, the genetic disease is muscular dystrophy.

Also provided is the use of compounds of Formula I and Formula II, a therapeutic or diagnostic agent and/or a suitable carrier in the preparation of a medicament. In some embodiments, the medicament is for the treatment of a genetic disease. In particular embodiments, the genetic disease is muscular dystrophy.

DETAILED DESCRIPTION

Figure 1:
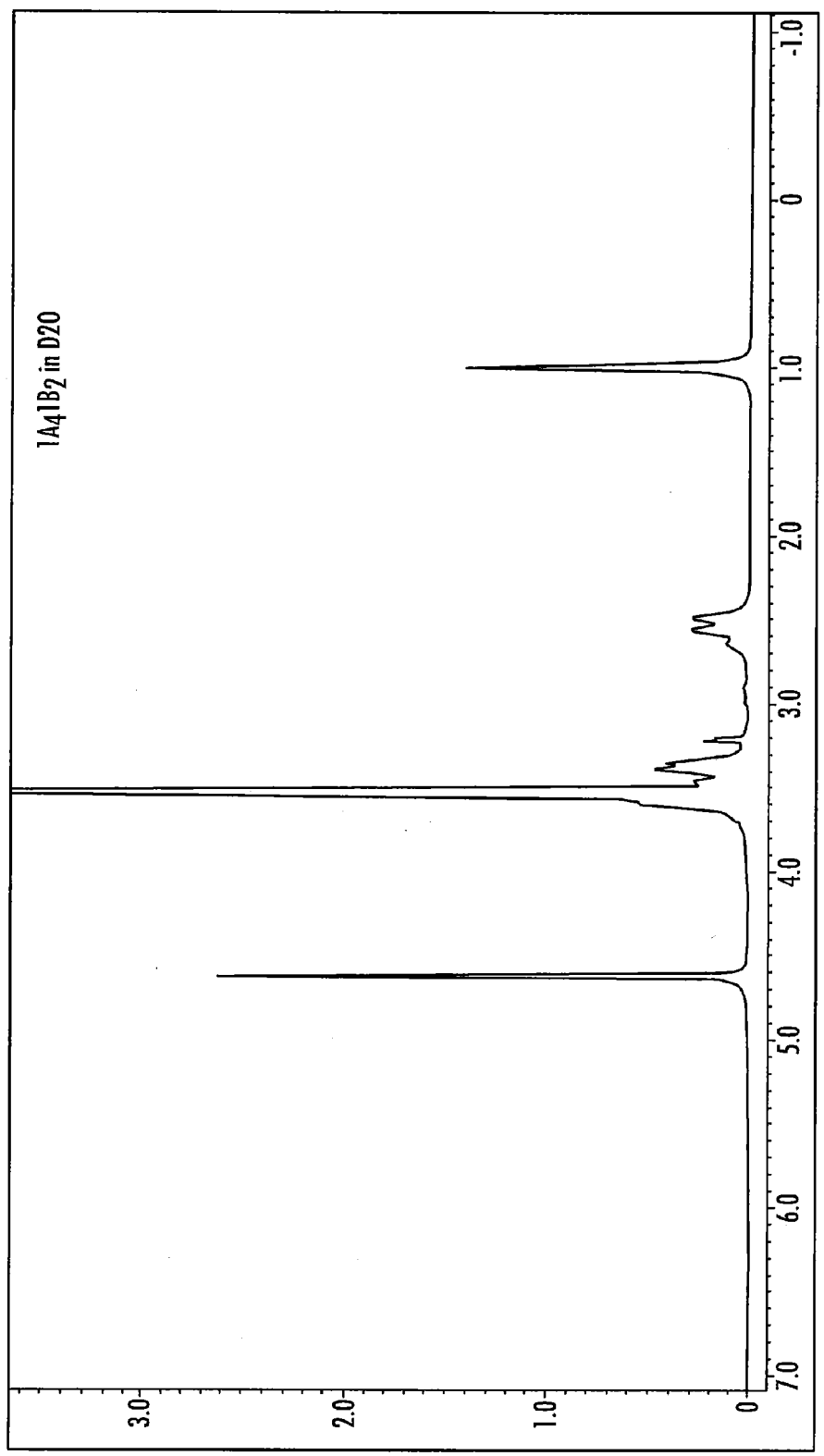
FIG. 1 depicts the $^1$H NMR spectrum obtained in $D_2O$ for 1A41B2 recorded on a JEOL ECA-500 NMR spectrometer.

Compounds as active agents of this invention include those described generally above, and are further described and/or illustrated by the embodiments, sub-embodiments, and species disclosed herein. As used herein, the following definitions shall apply unless otherwise indicated.

As described herein, compounds of the invention may optionally be substituted with one or more substituents, such as those illustrated generally above, or as exemplified by particular classes, subclasses, and species of the invention. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

As used herein, "a," "an" or "the" can mean one or more than one. Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a compound) and the like, is meant to encompass variations of ±20%, ±10%, ±5%, ±1%, ±0.5%, or even ±0.1% of the specified amount.

"Isomers" refer to compounds having the same number and kind of atoms and hence the same molecular weight, but differing with respect to the arrangement or configuration of the atoms.

"Stereoisomers" refer to isomers that differ only in the arrangement of their atoms in space.

"Diastereoisomers" refer to stereoisomers that are not mirror images of each other.

"Enantiomers" refers to stereoisomers that are non-superimposable mirror images of one another.

Enantiomers include "enantiomerically pure" isomers that comprise substantially a single enantiomer, for example, greater than or equal to about 90%, 92%, 95%, 98%, or 99%, or equal to about 100% of a single enantiomer.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of diastereomers, and substantially free of the opposite enantiomer, of the compound. A typical stereomerically pure compound comprises greater than about 80% by weight of one stereoisomer of the compound and less than about 20% by weight of the other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry. "Enantiomeric excess" (ee) of an enantiomer is [(the mole fraction of the major enantiomer) minus (the mole fraction of the minor enantiomer)]×100.

"Stable," as used herein, refers to compounds that are not substantially altered when subjected to conditions to allow for the production, detection, and preferably the recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"H" refers to a hydrogen atom. "C" refers to a carbon atom. "N" refers to a nitrogen atom. "O" refers to an oxygen atom. "S" refers to a sulfur atom.

"F" refers to a fluorine atom. "Cl" refers to a chlorine atom. "Br" refers to a bromine atom. "I" refers to an iodine atom.

"Alkyl," as used herein, refers to a straight or branched chain hydrocarbon containing from 1 or 2 to 10 or 20 or more carbon atoms (e.g., C2, C3, C4, C5, C6, C7, C8, C9, C10, C11, C12, C13, C14, C15, etc.). In some embodiments the alkyl can be a lower alkyl. "Lower alkyl" refers to straight or branched chain alkyl having from 1 to 3, or from 1 to 5, or from 1 to 8 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. In some embodiments, alkyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

As generally understood by those of ordinary skill in the art, "saturation" refers to the state in which all available valence bonds of an atom (e.g., carbon) are attached to other atoms. Similarly, "unsaturation" refers to the state in which not all the available valence bonds are attached to other atoms; in such compounds the extra bonds usually take the form of double or triple bonds (usually with carbon). For example, a carbon chain is "saturated" when there are no double or triple bonds present along the chain or directly connected to the chain (e.g., a carbonyl), and is "unsaturated" when at least one double or triple bond is present along the chain or directly connected to the chain (e.g., a carbonyl). Further, the presence or absence of a substituent depending upon chain saturation will be understood by those of ordinary skill in the art to depend upon the valence requirement of the atom or atoms to which the substituent binds (e.g., carbon).

"Alkenyl," as used herein, refers to a straight or branched chain hydrocarbon containing from 2 to 10 or 20 or more carbons, and containing at least one carbon-carbon double bond, formed structurally, for example, by the replacement of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. In some embodiments, alkenyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Alkynyl," as used herein, refers to a straight or branched chain hydrocarbon group containing from 2 to 10 or 20 or more carbon atoms, and containing at least one carbon-carbon triple bond. Representative examples of alkynyl include, but are not limited to, acetylenyl, 1-propynyl, 2-propynyl, 1-butynyl, 2-butynyl, 2-pentynyl, and the like. In some embodiments, alkynyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

The term "cycloalkyl," as used herein, refers to a saturated or unsaturated cyclic hydrocarbon group containing from 3 to 8 carbons or more. Representative examples of cycloalkyl include cyclopropyl, cyclobutyl, cyclobutenyl, cyclopentyl, cyclohexyl, cycloheptyl, and cyclooctyl. In some embodiments, cycloalkyl groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Heterocyclo," "heterocyclic" and "heterocycle" as used herein, refers to a monocyclic, bicyclic or tricyclic ring system. Monocyclic heterocycle ring systems are exemplified by any 3, 4, 5 or 6 membered ring containing 1, 2, 3, or 4 heteroatoms independently selected from the group consisting of: O, N, and S. The 5 member ring has from 0 to 2 double bonds, and the 6 member ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiomorpholine sulfoxide, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, pyranopyridine, quinoline, quinolizine, quinoxaline, quinazoline, tetrahydroisoquinoline, tetrahydroquinoline, thiopyranopyridine, and the like. In some embodiments, heterocyclo groups as described herein are optionally substituted (e.g., from 1 to 3 or 4 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Aryl" as used herein refers to a ring system having one or more aromatic rings. Representative examples of aryl include azulenyl, indanyl, indenyl, naphthyl, phenyl, tetrahydronaphthyl, and the like. The aryl groups of this invention can be optionally substituted with 1, 2, 3, 4, 5, 6 or 7 substituents independently selected from, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolinyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from the group consisting of: O, N, and S. The heteroaryl group, including each heteroatom, can be unsubstituted or substituted with from 1 to 4 suitable substituents, as chemically feasible. For example, the heteroatom S may be substituted with one or two oxo groups, which may be shown as =O. In some embodiments, heteroaryl groups as described herein are optionally substituted (e.g., from 1 to 3 or 4 times) with independently selected H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

An "acid" is a compound that can act as a proton donor or electron pair acceptor, and thus can react with a base. The strength of an acid corresponds to its ability or tendency to lose a proton. A "strong acid" is one that completely dissociates in water. Examples of strong acids include, but are not limited to, hydrochloric acid (HCl), hydroiodic acid (HI), hydrobromic acid (HBr), perchloric acid ($HClO_4$), nitric acid ($HNO_3$), sulfuric acid ($H_2SO_4$), etc. A "weak" or "mild" acid, by contrast, only partially dissociates, with both the acid and the conjugate base in solution at equilibrium. Examples of mild acids include, but are not limited to, carboxylic acids such as acetic acid, citric acid, formic acid, gluconic acid, lactic acid, oxalic acid, tartaric acid, ethylenediaminetetraacetic acid (EDTA), etc.

An "acid halide" as used herein refers to an organic functional group having a carbonyl group (C=O) linked to a halogen.

An "acyl group" is intended to mean a group —C(O)R, where R is a suitable substituent (for example, an acyl group may be an acetyl group (—C(O)CH$_3$), a propionyl group, a butyroyl group, a benzoyl group, or an alkylbenzoyl group).

"Aliphatic" is an acyclic or cyclic, non-aromatic carbon compound.

"Alkoxy," as used herein, refers to an alkyl, alkenyl, alkynyl, aryl, cycloalkyl, heterocyclo, or heteroaryl group, as defined herein, appended to the parent molecular moiety through an oxy group, as defined herein. Representative examples of alkoxy include, but are not limited to, methoxy, ethoxy, propoxy, phenoxy, 2-propoxy, butoxy, tert-butoxy, pentyloxy, hexyloxy and the like. In some embodiments, alkoxy groups as described herein are optionally substituted (e.g., from 1 to 3 or 5 times) with independently selected, but not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

"Amidino" as used herein, refers to the —C(=NH)NH$_2$ moiety. "Optionally substituted" amidino refers to the NH and NH$_2$ groups wherein none, one, two or three of the hydrogens is replaced by a suitable substituent as described herein, such as alkyl, alkenyl, alkynyl, cycloalkyl, heterocyclo, aryl, heteroaryl, alkoxy, carbonyl, carboxy, etc.

An "amine" or "amino" is intended to mean the group —NH$_2$. "Optionally substituted" amines refers to —NH$_2$ groups wherein none, one or two of the hydrogens is replaced by a suitable substituent as described herein, such as alkyl, alkenyl, alkynyl, cycloalkyl, heterocyclo, aryl, heteroaryl, alkoxy, carbonyl, carboxy, etc. In some embodiments, one or two of the hydrogens are optionally substituted with independently selected, but not limited to, halo, hydroxy, acyl, alkyl, alkenyl, alkynyl, cycloalkyl, heterocyclo, aryl, heteroaryl, alkoxy, amino, amide, thiol, ester, sulfone, sulfoxide, oxo, oxy, nitro, carbonyl, carboxy, amino acid and peptide. Disubstituted amines may have substituents that are bridging, i.e., form a heterocyclic ring structure that includes the amine nitrogen.

An "amine," "organic amine," "amine base" or "organic amine base" as used herein refers to an organic compound having a basic nitrogen atom (R—NR'R"), and may be a primary (R—NH$_2$), secondary (R—NHR') or tertiary (R—NR'R") amine. R, R' and R" may be independently selected from the group consisting of alkyl (e.g., cycloalkyl), aryl and heteroaryl, which groups may be optionally substituted, or R and R', R and R" and/or R' and R", when present, may also combine to form cyclic or heteroalicyclic ring. In some embodiments the amine is aromatic. Examples of aromatic amines include, but are not limited to, pyridine, pyrimidine, quinoline, isoquinolines, purine, pyrrole, imidazole, and indole. The aromatic amines may be substituted or unsubstituted. Examples of amines include, but are not limited to, triethylamine, pyridine, dimethylaminopyridine, N-methylmorpholine, Hunig's base (N,N-diisopropylethylamine), and 1,8-diazabicyclo[5.4.0] undec-7-ene (DBU).

An "amide" as used herein refers to an organic functional group having a carbonyl group (C=O) linked to a nitrogen atom (N), or a compound that contains this group, generally depicted as:

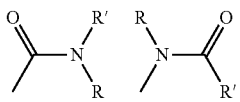

wherein, R and R' can independently be any covalently-linked atom or atoms, for example, H, halo, hydroxy, acyl, alkyl, alkenyl, alkynyl, cycloalkyl, heterocyclo, aryl, heteroaryl, alkoxy, amino, amide, sulfone, sulfoxide, carboxy, amino acid and peptide.

An "amide coupling agent" is an agent that may be used to couple a nitrogen and carboxyl group to form an amide, typically by activating the carboxyl group. Examples of amide coupling agents include, but are not limited to, carbodiimides such as N,N'-dicyclohexylcarbodiimide (DCC), N-(3-dimethylaminopropyl)-N'ethylcarbodiimide (EDC) or N-(3-dimethylaminopropyl)-N-ethylcarbodiimide hydrochloride (EDAC), N,N'-diisopropylcarbodiimide (DIC); imidazoliums such as 1,1'-carbonyldiimidazole (CDI), 1,1'-carbonyl-di-(1,2,4-triazole) (CDT); uronium or guanidinium salts such as O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU), and O-(benzotriazol-1-yl)-N,N,N',N'-tetramethyluronium tetrafluoroborate (TBTU); phosphonium salts such as benzotriazol-1-yloxy)tris(dimethylamino)phosphonium hexafluorophosphate (BOP or Castro's reagent), (benzotriazol-1-yloxy)tripyrrolidinophosphonium hexafluorophosphate (PyBOP®, Merck KGaA, Germany), 7-azabenxotriazol-1-yloxy)tripyrrolidinophosphonium hexafluorophosphate (PyAOP); alkyl phosphonic acid anhydrides such as T3P® (Archimica, Germany), etc. In another embodiment the carboxyl group may be activated by forming an acid halide or acid anhydride with an agent including but not limited to thionyl chloride, phosphorus pentachloride, and phosphorus trichloride.

"Amino acid side chain" as used herein refers to any of the 20 commonly known groups associated with naturally-occurring amino acids, or any natural or synthetic homologue thereof. An "amino acid" includes the sidechain group, the amino group, alpha-carbon atom, and carboxy groups, as commonly described in the art. Examples of amino acids include glycine, and glycine that is substituted with a suitable substituent as described herein, such as alkyl, alkenyl, alkynyl, cycloalkyl, heterocyclo, aryl, heteroaryl, alkoxy, carbonyl, carboxy, etc., or a pharmaceutically acceptable salt or prodrug thereof. For example, "Histidine" is one of the 20 most commonly known amino acids found naturally in proteins. It contains a —(CH$_2$)-imidazole side chain substituent. Other examples of naturally-occurring amino acids include lysine, arginine, aspartic acid, glutamic acid, asparagine, glutamine, serine, threonine, tyrosine, alanine, valine, leucine, isoleucine, phenylalanine, methionine, tryptophan, and cysteine. Also included in the definitions of "amino acid sidechain" and "amino acid" is proline, which is commonly included in the definition of an amino acid, but is technically an imino acid. As used in this application, both the naturally-occurring L- and the non-natural D-amino acid enantiomers are included. The single letter code for amino acids is A (Ala), C (Cys), D (Asp), E (Glu), F (Phe), Q (Gly), H (His), I (Ile), K (Lys), L (Leu), M (Met), N (Asn), P (Pro), Q (Gln), R (Arg), S (Ser), T (Thr), V (Val), W (Trp), and Y (Tyr).

"Aqueous" is a solution in which water is the dissolving medium, or solvent. An "aqueous base" is a base in water. An "aqueous acid" is an acid in water.

"Araalkyl," as used herein, refers to an alkyl group that has an aryl group appended thereto, for example benzyl and naphthylmethyl groups.

"Azido," as used herein, refers to the —N$_3$ functional group.

A "base" is a compound that can accept a proton (hydrogen ion) or donate an electron pair. A base may be organic (e.g., DBU, cesium carbonate, etc.) or inorganic. A "strong base" as used herein is a compound that is capable of deprotonating very weak acids. Examples of strong bases include, but are not limited to, hydroxides, alkoxides, and ammonia.

"Carbonate," as used herein refers to a —O(CO$_2$)R functional group wherein R is for example, alkyl, alkenyl, alkynyl, cycloalkyl, heterocyclo, aryl and heteroaryl that may be optimally substituted.

"Carbonyl" is a functional group having a carbon atom double-bonded to an oxygen atom (C=O).

"Carboxy" and "carboxylic acid" as used herein refers to a —COOH functional group, also written as —CO$_2$H or —(C=O)—OH.

"Cyano" refers to the group —C≡N, or —CN.

A "diamine" as used herein refers to an organic compound comprising two primary amines. Examples include, but are not limited to, (1R,2R)-cyclohexane-1,2-diamine, (1S,2S)-cyclohexane-1,2-diamine, 3,3'-(piperazine-1,4-diyl)bis(propan-1-amine), ethane-1,2-diamine, propane-1,3-diamine, N$^1$-(3-aminoproyl)propane-1,3-diamine, N$^1$-(2-aminoethyl)ethane-1,2-diamine, N$^1$,N$^{1'}$-(ethane-1,2-diyl)bis(ethane-1,2-diamine), N$^1$-(2-aminoethyl)-N$^2$-(2-((2-aminoethyl)amino)ethyl)ethane-1,2-diamine, N$^1$,N$^{1'}$-(ethane-1,2-diyl)bis(N$^2$-(2-aminoethyl)ethane-1,2-diamine),

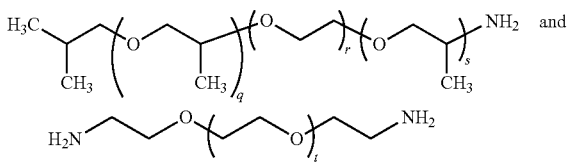

wherein q=0-100, r=1-100, s=0-100 and t=1-200.

A "diol" as used herein refers to an organic compound comprising two hydroxyl groups. Diols such as lipoloxamers and poloxamers useful as biocompatible amphiphiles in an amphiphilic cationic polymer of the invention can have a formula selected from the group consisting of:

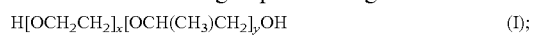

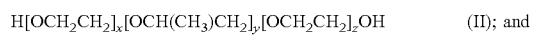

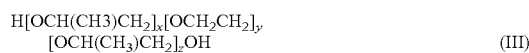

wherein x, y, and z each have a value from about 5 to about 80. Preferably, x, y, and z each have a value from about 10 to about 65, about 15 to about 55, or about 20 to about 50. Persons skilled in the art will understand that formulas (I) through (III) are oversimplified in that, in practice, the orientation of the isopropylene radicals may be random.

"Ester" as used herein refers to a —COOR functional group, also written as—CO$_2$R or —(C=O)—OR wherein, R is for example, alkyl, alkenyl, alkynyl, cycloalkyl, heterocyclo, aryl and heteroaryl that may be optimally substituted.

"Form a ring" as used herein with respect to two substituents, e.g., $R^7$ and $R^8$ together forming a ring, refers to the two groups being linked together via one or more atoms (e.g., carbon) to form ring atoms making up a cycloalkyl, heterocyclo, aryl or heteroaryl as described herein. Rings may be part of a monocyclic, bicyclic or tricyclic moiety, each of such ring(s) being a saturated or unsaturated member of the monocyclic, bicyclic or tricyclic moiety.

"Formylated," as used herein, refers to a chemical reaction that introduces a formyl group (methanoyl, —CHO) into an organic molecule.

"Formyl" or "formyl group", as used herein, refers to a —CHO moiety.

"Halo" refers to F, Cl, Br or I.

"Hydroxy," as used herein, refers to an HO— moiety.

A "hydroxide" is the commonly known anion HO⁻, or a salt thereof (typically an alkali metal or alkaline earth metal salt thereof). Examples of hydroxides include, but are not limited to, sodium hydroxide (NaOH), potassium hydroxide (KOH), lithium hydroxide (LiOH), and calcium hydroxide (Ca(OH)$_2$).

An "inorganic" compound is a compound not containing carbon.

A "linker," as used herein, refers to a group of atoms that are bonded to two discrete compounds, typically organic compounds. The linker can be a non-biodegradable linker. As illustrated below a $C_4H_8$ group of atoms functions as a linker bonded to a triazine and benzene ring.

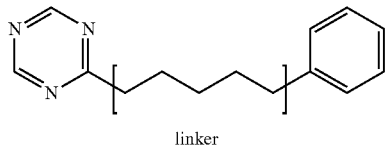

linker

The term "oxo", as used herein, refers to a =O moiety.
The term "oxy", as used herein, refers to a —O— moiety.

"Nitro" refers to the organic compound functional group —NO$_2$.

A "thiol" or "mercapto" refers to an —SH group, its tautomer =S or —SR wherein, R is for example alkyl, alkenyl, alkynyl, cycloalkyl, heterocyclo, aryl and heteroaryl that may be optimally substituted.

A "sulfone" as used herein refers to a sulfonyl functional group, generally depicted as:

wherein, R can be any covalently-linked atom or atoms, for example, H, halo, hydroxy, alkyl, alkenyl, alkynyl, cycloalkyl, heterocyclo, aryl, heteroaryl, alkoxy, amino, amino acid and peptide.

A "sulfoxide" as used herein refers to a sulfinyl functional group, generally depicted as:

wherein, R can be any covalently-linked atom or atoms, for example, H, halo, hydroxy, alkyl, alkenyl, alkynyl, cycloalkyl, heterocyclo, aryl, heteroaryl, alkoxy, amino, amino acid and peptide.

The term "optionally substituted" indicates that the specified group is either unsubstituted or substituted by one or more suitable substituents. A "substituent" is an atom or group which takes the place of a hydrogen atom on the parent chain or cycle of an organic molecule, examples include, but are not limited to, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol. In some embodiments, the substituent may be further substituted. For example, an atom or group which takes the place of a hydrogen atom on the substituent; examples include, but are not limited to, H, acyl, alkyl, alkenyl, alkoxy, alkynyl, amidino, amino, amino acid, amide, aryl, azido, carbonate, carbonyl, carboxy, cyano, cycloalkyl, ester, formyl, halo, heterocyclo, heteroaryl, hydroxy, nitro, oxo, oxy, peptide, sulfone, sulfoxide, and thiol.

An "organic" compound as used herein is a compound that contains carbon.

An "organic solvent" is a compound containing carbon that is useful as a solvent. Examples of organic solvents include, but are not limited to, acid amides such as N,N-dimethylformamide and N,N-dimethylacetamide; alcohols such as ethanol, methanol, isopropanol, amyl alcohol, ethylene glycol, propylene glycol, 1-butanol, butyl carbitol acetate and glycerin; aliphatic hydrocarbons such as hexane and octane; aromatic hydrocarbons such as toluene, xylenes and benzene; ketones such as acetone, methyl ethyl ketone and cyclohexanone; halogenated hydrocarbons such as dichloromethane, chlorobenzene and chloroform; esters such as ethyl acetate, amyl acetate and butyl acetate; ethers such as tetrahydrofuran, 2-methyltetrahydrofuran, 1,4-dioxane, tert-butyl methyl ether, diethyl ether and ethylene glycol dimethyl ether; nitriles such as acetonitrile; and sulfoxides such as dimethylsulfoxide.

An "oxidizing agent" is an agent useful to oxidize a compound, whereby the compound loses electrons or increases its oxidation state. Examples include, but are not limited to, oxygen, ozone, organic peroxides such as hydrogen peroxide, halogens such as fluorine or chlorine, or halogen compounds such as chlorite, chlorate or perchlorate, nitrate compounds such as nitric acid, a sulfuric acid or persulfuric acid, hypohalite compounds such as hypochlorite and sodium hypochlorite (NaOCl), hexavalent chromium compounds such as chromic and dichromic acids and chromium trioxide, pyridinium chlorochromate and chromate/dichromate compounds, permanganate compounds, sodium perborate, nitrous oxide, silver oxide, osmium tetroxide, Tollens' reagent, and 2,2'-dipyridyldisulfide.

Organic cations suitable for use in the amphiphilic cationic polymers of the invention include, but are not limited to amines, including polyamines, such as linear or branched polyalkylenimines (e.g., polyethylenimine (PEI), polypropylenimine (PPI), etc.). Preferably, the organic cation is a low molecular weight polyalkylenimine. As used herein, a "low molecular weight polyalkylenimine" is a polyalkylenimine having a molecular weight of 5,000 Da or less. For example, the low molecular weight polyalkylenimine can be branched polyethylenimine having a molecular weight between 200 to 3000, preferably 3000 Da or lower. Exemplary low molecular weight polyethylenimines include PEI-2 k (2000 Da), PEI-1.2 k (1200 Da), and PEI-0.8 k (800 Da) Alternatively, the low molecular weight polyalkylenimine can be branched polypropylenimine having a molecular weight between 200 to 5000, preferably 4000 Da or less.

Additional organic cations suitable for use in the amphiphilic cationic polymers of the invention include dendrimers, and polypeptides (e.g., poly-L-arginine, poly-L-lysine, or a mixture of arginine and lysine). Suitable dendrimers can be formed from diamines such as 1,2-ethanediamine, 1,3-propanediamine, 1,4-butanediamine, etc. Preferably, the dendrimer, or polypeptide has a molecular weight of about 4000 Da or less. For example, preferred dendrimers include DAB-dendr-(NH2)x (see structure, below); and preferred polypeptides include poly-L-lysine and poly-L-arginine, each having a molecular weight of about 500 Da to about 2000 Da.

Other organic cations suitable for use in the amphiphilic cationic polymers of the invention include amines. As used herein, an amine is an amine having a molecular weight of 1000 Da or less. Preferably, the low molecular weight amine has a molecular weight of about 500 Da or less. The low molecular weight amine can be linear or cyclic and preferably includes two or more amines (e.g., two or more primary, secondary, or tertiary amines, or any combination thereof). Low molecular weight amines useful as organic cations include, but are not limited to, amines having one of the following structures:

The term "PEI" or "polyethylenimine" as used herein, refers to a "polyethylenimine" having the chemical structure as shown below, including linear, branched and dendrimer structures:

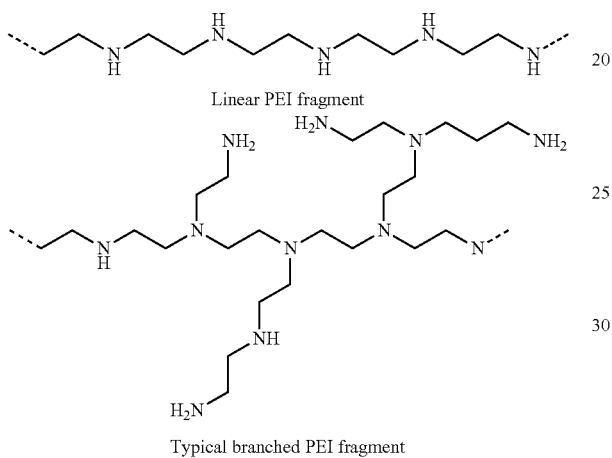

Linear PEI fragment

Typical branched PEI fragment

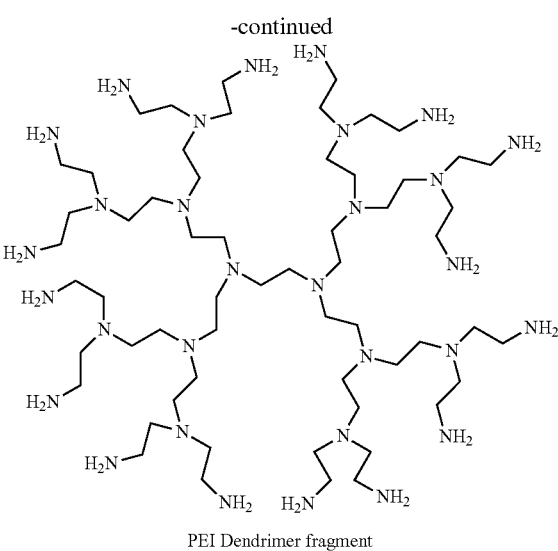

PEI Dendrimer fragment

The PEIs of the present invention range in molecular weight from about 400 to about 10,000. In some embodiments, the molecular weight is from about 500 to 3000.

Additional low molecular weight amines useful as organic cations include tetrakis(3-aminopropyl)-1,3-propanediamine and tris(3-aminopropyl)amine (see structures, below). Other suitable low molecular weight amines will be obvious to persons skilled in the art.

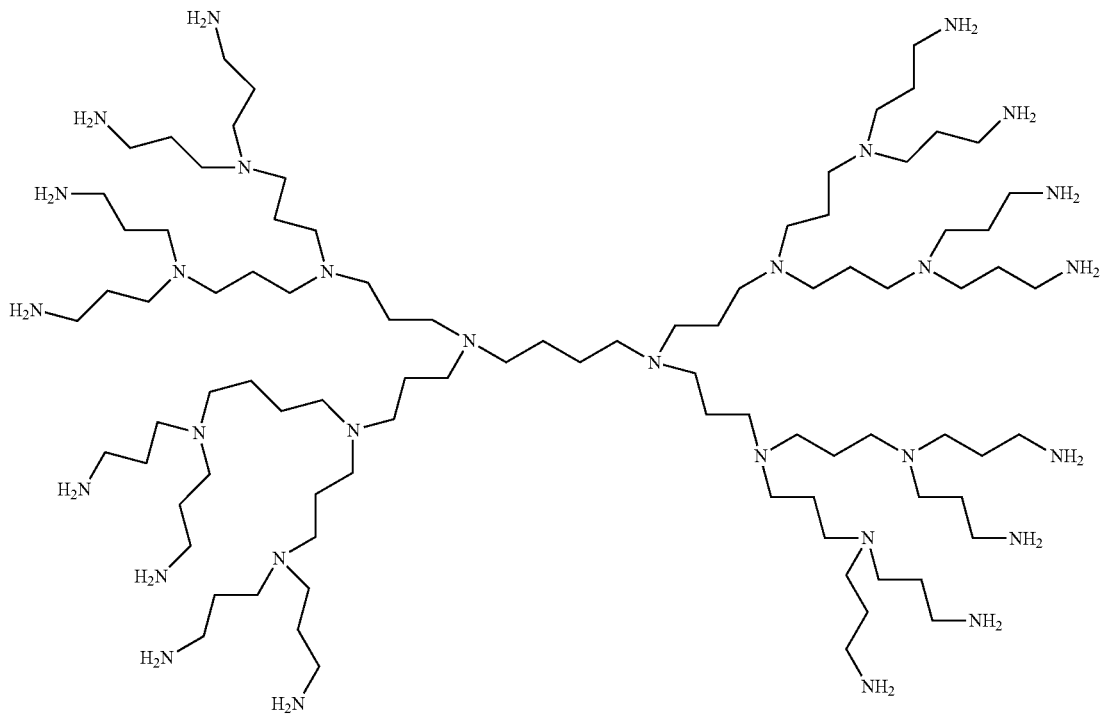

DAB-dendr-(NH$_2$)x

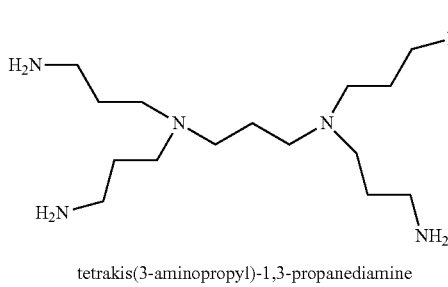
tetrakis(3-aminopropyl)-1,3-propanediamine

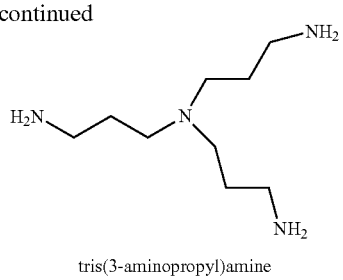
tris(3-aminopropyl)amine

A "peptide" is a linear chain of amino acids covalently linked together, typically through an amide linkage, and contains from 1 or 2 to 10 or 20 or more amino acids, and is also optionally substituted and/or branched.

A "pharmaceutically acceptable salt" is intended to mean a salt that retains the biological effectiveness of the free acids and bases of a specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propionates, oxalates, malonates, succinates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methane-sulfonates, propanesulfonates, naphthalene-1-sulfonates, naphthalene-2-sulfonates, and mandelates.

The term PLL, or "polylysine" as used herein, refer to compounds having the chemical structure:

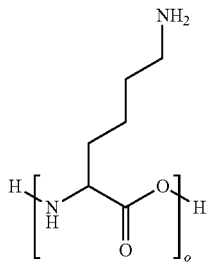

wherein o ranges from about 5 to about 50. In the present application, the polylysines range in molecular weight from about 500 to about 5,000, and 1000 to 1500 in some embodiments.

The term "PMO" as used herein, refers to compounds having the general structure:

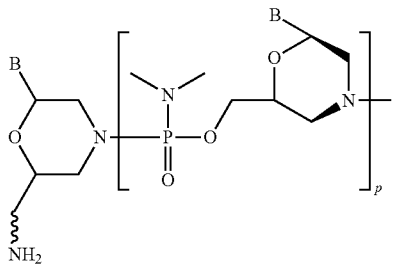

wherein B comprises a pyrimidine or purine and p ranges from about 15 to about 40, and in some embodiments, 20 to 30.

A "prodrug" is intended to mean a compound that is converted under physiological conditions or by solvolysis or metabolically to a specified compound that is pharmaceutically active. A thorough discussion is provided in T. Higuchi and V. Stella, Prodrugs as Novel delivery Systems, Vol. 14 of the A.C.S. Symposium Series and in Edward B. Roche, ed., Bioreversible Carriers in Drug Design, American Pharmaceutical Association and Pergamon Press, 1987, both of which are incorporated by reference herein in their entirety.

"Protecting group" as used herein, is meant that a particular functional moiety, e.g., O, S, or N, is temporarily blocked so that a reaction can be carried out selectively at another reactive site in a multifunctional compound. For example, in certain embodiments, as detailed herein, certain exemplary oxygen protecting groups are utilized. Oxygen protecting groups include, but are not limited to, groups bonded to the oxygen to form an ether, such as methyl, substituted methyl (e.g., Trt (triphenylmethyl), MOM (methoxymethyl), MTM (methylthiomethyl), BOM (benzyloxymethyl), PMBM or MPM (p-methoxybenzyloxymethyl)), substituted ethyl (e.g., 2-(trimethylsilyl)ethyl), benzyl, substituted benzyl (e.g., para-methoxybenzyl), silyl (e.g., TMS (trimethylsilyl), TES (triethylsilyl), TIPS (triisopropylsilyl), TBDMS (t-butyldimethylsilyl), TBDPS (t-butyldiphenylsilyl), 2-trimethylsilylprop-2-enyl, t-butyl, tetrahydropyranyl, allyl, etc.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The terms "nucleotide sequence" "nucleic acid," "nucleic acid molecule," "oligonucleotide" and "polynucleotide" are also used interchangeably herein to refer to a heteropolymer of nucleotides and are presented herein in the 5' to 3' direction, from left to right and are represented using the standard code for representing the nucleotide characters as set forth in the U.S. sequence rules, 37 CFR §§1.821-1.825 and the World Intellectual Property Organization (WIPO) Standard ST.25. The term polynucleotide, nucleotide sequence, or nucleic acid refers to a chain of nucleotides without regard to length of the chain, unless otherwise specified. It will also be understood that DNA nucleotide sequence, nucleic acid, nucleic acid molecule, oligonucleotide and polynucleotide, may represent a corresponding RNA nucleotide sequence, nucleic acid, nucleic acid molecule, oligonucleotide and polynucleotide, wherein the thymine (T) base in the DNA nucleotide sequence, nucleic acid, nucleic acid molecule, oligonucleotide and polynucleotide is replaced with uracil (U) in the RNA nucleotide sequence, nucleic acid, nucleic acid molecule, oligonucleotide and polynucleotide.

"Amphiphilic" refers to the ability to dissolve in both water and lipids, i.e., hydrophobic and hydrophilic qualities. The terms "amphiphilic moiety" and "amphipile" mean a moiety which is amphiphilic and/or which, when attached to a moiety, increases the amphiphilicity of the resulting conjugate.

"Polycation" refers to molecules with multiple groups that are positively charged or capable of being positively charged under physiological or acidic conditions.

"Cationic peptide" or "Cell penetrating peptides" (CPPs) refer to amino acid compositions that either include a high relative abundance of positively charged amino acids such as lysine or arginine or have sequences that include an alternating pattern of polar/charged amino acids and non-polar, hydrophobic amino acids. These two types of structures are referred to as polycationic or amphipathic, respectively. A third class of CPPs are the hydrophobic peptides, including only apolar residues, with low net charge or have hydrophobic amino acid groups that are involved in cellular uptake.

"Effective amount" as used herein refers to an amount of a compound, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

By the term "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. Treat does not necessarily indicate a cure.

A "treatment effective" amount as used herein is an amount that is sufficient to treat (as defined herein) the subject. Those skilled in the art will appreciate that the therapeutic effects need not be complete or curative, as long as some benefit is provided to the subject.

"Therapeutic" refers to an agent, drug, compound, composition or the like that imparts a desired biological, physiological and/or pharmacological effect, which need not be complete or curative, as long as some benefit is provided.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the term "prevent," "preventing," or "prevention of" (and grammatical variations thereof) refer to prevention and/or delay of the onset and/or progression of a metabolic disease in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

"Diagnostic" refers to the use of information (e.g., genetic information or data from other molecular tests on biological samples, signs and symptoms, physical exam findings, cognitive performance results, etc.) to anticipate the most likely outcomes, timeframes, and/or response to a particular treatment for a given disease, disorder, or condition, based on comparisons with a plurality of individuals sharing common nucleotide sequences, symptoms, signs, family histories, or other data relevant to consideration of a subject' health status. Accordingly, as "diagnostic agent" refers to a molecule, agent, drug, compound, composition or the like that allows one to obtain and/or use the information referenced above.

Amphiphilics are able to interact with cell membranes and enhance cell membrane uptake, and can raise the effective concentration of plasmid/oligos to the target cells by at least preventing nonspecific binding of cargo plasmid/oligos to charged extracellular components. The selected amphiphilic polymers herein are biocompatible. Therefore, cationic amphiphilic copolymers can acquire both the ability to bind and condense DNA/oligonucleotides and to enhance the interactions with cell membranes, and thus potentially improving delivery efficiency significantly. Amine-PEGa-mine, ($NH_2$—PEG-$NH_2$), Mw 1,000-40,000 mPEG-$NH_2$, Mw: 1000-40,000, 4 and 8 arm PEGamines (Mw: 5 k-10 k, 10 k-40 k) and JEFFAMINE® Polyetheramines, as the amphiphilic segment grafted onto the triazine core: The JEFFAMINE® Polyetheramines are generally composed of ethylene oxide (EO) and propylene oxide (PO) in different ratios and can include active primary amine groups with lower toxicity. Historically, the JEFFAMINE® Polyetheramine family consisted of monoamines, diamines, and triamines based on the core structure. Suitable JEFFAMINE® Monoamines have the following structures:

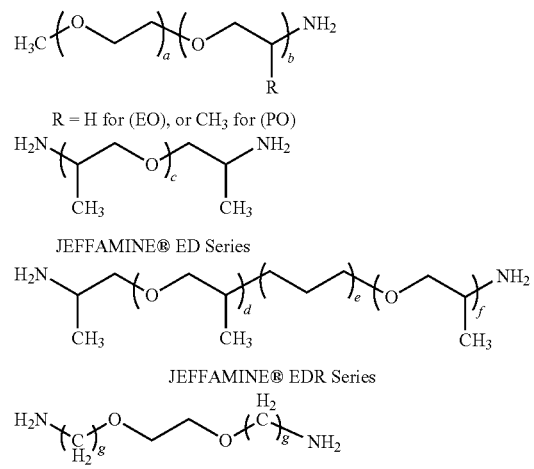

wherein a has an average value of about 2 to about 30, and wherein b has an average value of about 1 to about 40, wherein c has an average value of about 2 to about 80, wherein d+f has an average value of about 2 to about 100, wherein e has an average value of about 2 to about 100, wherein g has an average value of about 2 to about 30, Preferred Jeffamines include M-600(XTJ-505) (PPO:PEO mol ratio 9:1; MW~600), M-1000(XTJ-506) (PPO:PEO mol ratio 3:19; MW~1000), M-2005 (PPO:PEO mol ratio 29:6; MW~2000), and M-2070 (PPO:PEO mol ratio 10:31; MW~2000), D-400 (MW~430), D-2000 (MW~2000), D-4000 (MW~4000), ED-600 (MW~600), ED-900 (MW~900), ED-2000 (MW~2000), EDR-148, EDR-176, and XJT-435. Polymeric monoamines, diamines, and triamines are commercially available with different molecular weights and HLBs. These compounds provide a basis for design of new compounds as provided herein.

Embodiments of the present invention provide novel amphiphilic cationic polymers and their use as delivery vehicles for nucleic acids and their analogues, including but not limited to, plasmid DNA, synthetic DNA and RNA sequences, chemically modified DNA and RNA as antisense oligonucleotides and short interfering RNA (siRNA), in vitro and in vivo for experimental purposes and treating human diseases.

In particular, the present invention provides a series of triazine-cored amphiphilic cationic copolymers as well as polymer-oligonucleotide conjugates. Chemical conjugation of the polymers to AO, such as phosphorodiamidate morpholino oligomer (PMO) can be more efficient and the complexes can have less toxicity compared with conventional polymer conjugates.

The physicochemical properties, toxicity, and application of the compositions of matter of the present invention in vitro were investigated. Further, conjugates were administered into the muscles of dystrophic mdx mice and their effects were studied. In some embodiments, polymers were condensed with pDNA/AQs and formed stable complexes with desirable molecular weights. In particular embodiments, polyplexes showed remarkably low cytotoxicity in comparison to PEI 25 k in the CHO, C2C12, H4IIE, and HSK cell lines. In one aspect, no cell death occurred even at the dose of 20 micrograms/ml whereas 5 micrograms/ml PEI 25 k caused more than 50% cell death.

In particular embodiments of the invention, the ratio for the polymer/nucleic acid, for example, polymer/DNA or polymer/AOs is determined. The efficiency of the polymers for gene and AOs delivery includes consideration of the polymer size, HLB and charge density, as well as the nucleic acid size and charges. Generally, the ratio (w/w) of polymer/pDNA or AO to achieve a generally effective delivery may be in the range of 1-100, with non-detectable toxicity, for some embodiments. In some embodiments, the range should be about 5-20.

In some of the embodiments of the present invention, polymers can be used for gene delivery, such as plasmid/or synthetic DNA sequence-based transgene or AOs delivery for exon-skipping to treat muscular dystrophy, for example, Duchenne Muscular Dystrophy. In mouse models, polymer-treated pDNA induced 5-10 fold higher positive fibers than pDNA only, and the standard PEI 25K showed higher toxicity even at low doses.

In another embodiment, PMO is complexed with compounds of Formula I or II. Such complexes may enhance PMO-induced exon-skipping of the dystrophin gene. Such techniques have been shown to be effective for restoring the expression of dystrophin protein in Duchenne muscular dystrophy patients who lack dystrophin expression due to mutations of the gene.

In further embodiments, compounds of Formula I or II were used as carriers for hydrophobic anticancer drugs. The hydrophilic moiety in a compound of Formula I or II, such as PEO, may prevent cell adhesion, for example, by ectopically driven steric repulsion and increasing the hydrophilicity of carrier surfaces.

In another embodiment, compounds of Formula I or II can be used as vaccine carriers for antigenic proteins. For example, no satisfactory protein delivery methods are available currently to transport immunogens across mucosal barriers, i.e., nasal and intestinal mucosa. The compounds of Formula I and II at least in view of their nanosize and positive charge, as well as their hydrophobicity, which is suitable for cell uptake and enhanced absorption across nasal mucosa, may be useful in protein delivery.

It is generally unexpected that low MW polyamines, when combined with amphiphiles can achieve highly effective delivery of plasmid DNA and oligonucleotides in both cell culture and in muscles in vivo. PMO is chemically charge-neutral, and therefore, it is not expected to bind effectively to a polycationic amphiphile. However, exon-skipping enhancement was achieved with the use of the Compounds of Formulas I and II for the delivery of PMO both in cell culture and in vivo.

The results obtained from using the compositions of matter of the present invention demonstrate that the compounds of Formula I and II have lower toxicity when compared with PEI 25 k, lipofectamine, as well as the commercial control Endoporter (for PMO delivery in vitro). The formulation of polymer/pDNA or AOs are composed of polymer and bioactive agents only. Some of these polymers have demonstrated effective transgene efficiency or enhanced exon-skipping compared with a positive control. The moderate HLB and middle-sized amphiphiles showed higher potent efficacy for DNA or AOs delivery in vitro and in vivo for treating diseases from infections to genetic disorders.

In particular embodiments, cationic components may include small amines, polyamines and cationic peptides/cell-penetrating peptides.

Small amines: Such as

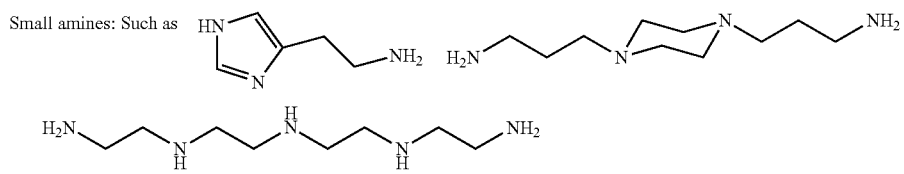

Cationic peptides (Mw = 500-25,000 Da); Cell-penetrating peptides (CPPs)
Such as: Poly-asparagine, Poly-histidine, Poly-arginine, Poly-lysine.

-continued

Polyamines: Such as Polyethlyemines or Polypropylene imines (Mw = 500-15,000 Da) including linear, branched an ddendrimer structures.

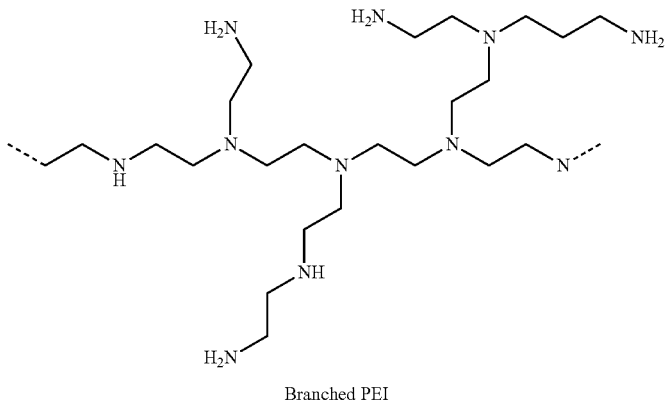

Branched PEI

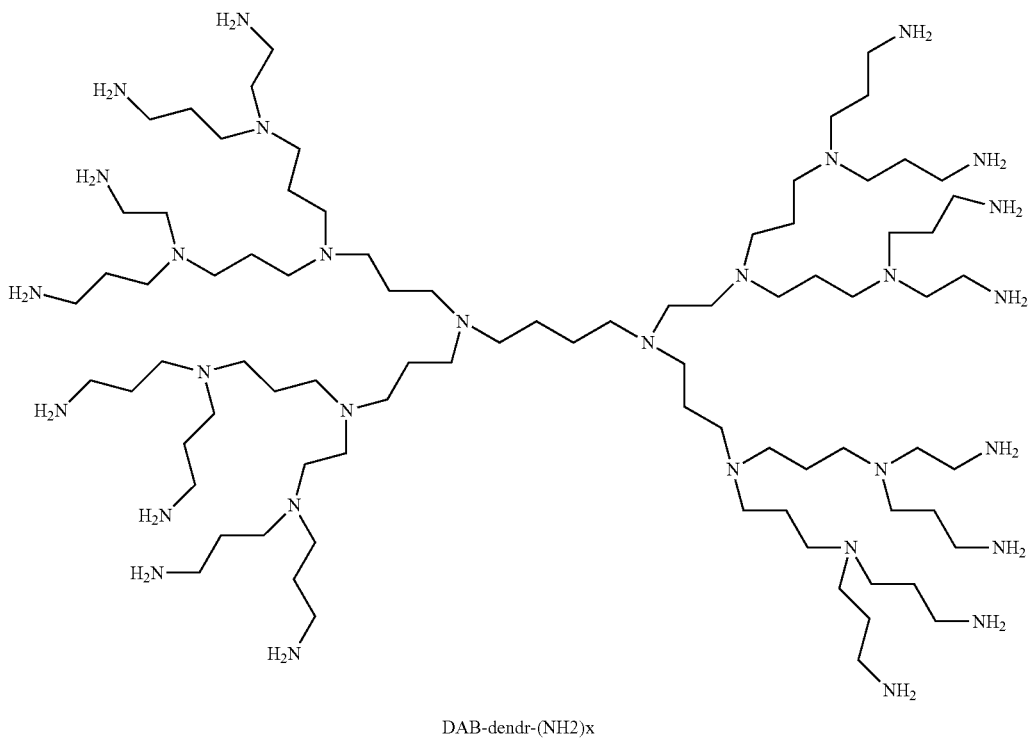

DAB-dendr-(NH2)x

In some embodiments, biocompatible/amphiphilic components may include those such as amine-terminated PEG, Jefferamine series, polysorbate series, poloxamers, lipoloxamers.

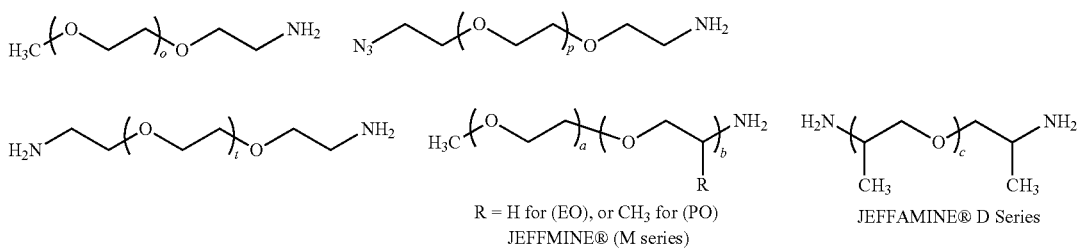

R = H for (EO), or $CH_3$ for (PO)
JEFFMINE® (M series)

JEFFAMINE® D Series

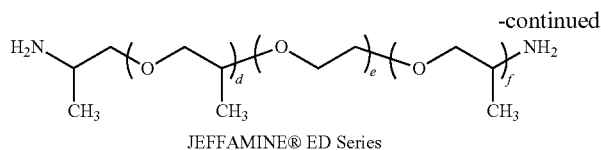

JEFFAMINE® ED Series

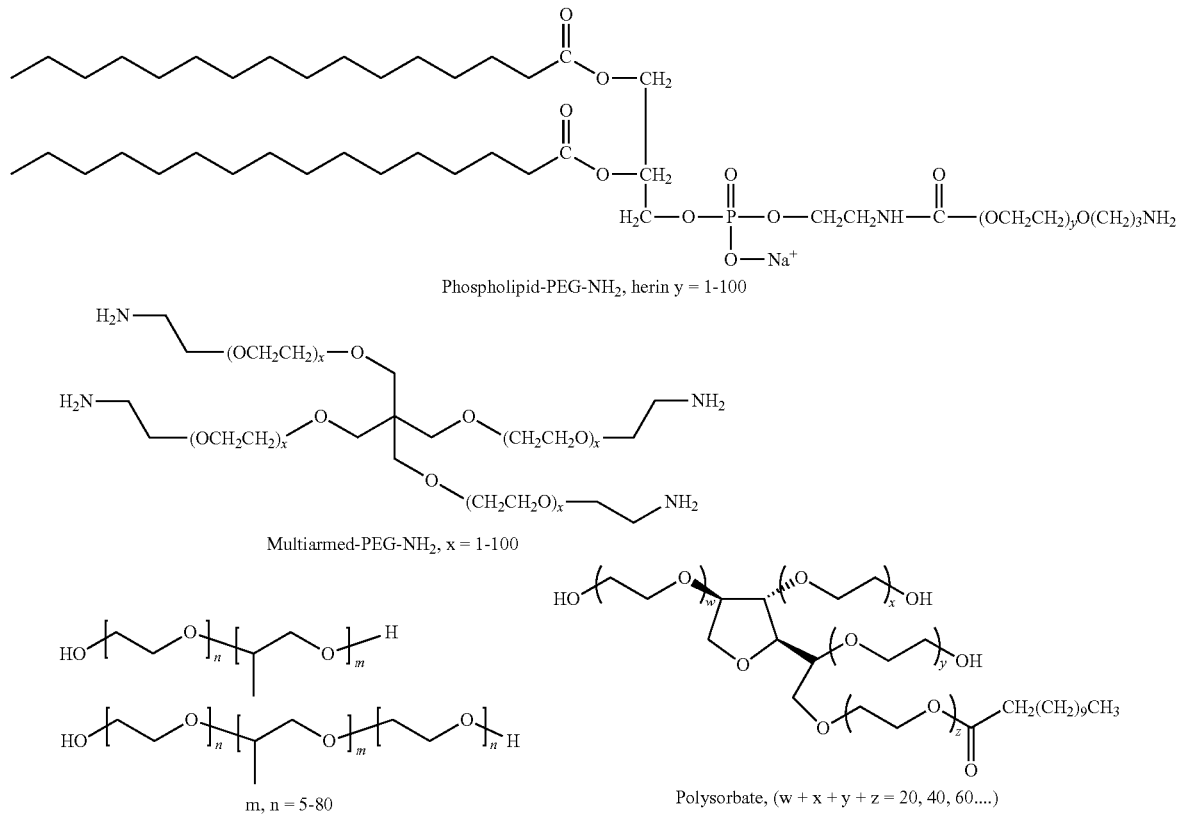

Phospholipid-PEG-NH$_2$, herin y = 1-100

Multiarmed-PEG-NH$_2$, x = 1-100 m, n = 5-80

Polysorbate, (w + x + y + z = 20, 40, 60....)

In some embodiments, the therapeutic and/or diagnostic agent (Mw=1,000-20,000) include those such as, plasmid DNA (pDNA), DNA sequences, RNA sequences, siRNA, antisense oligonucleotides, nucleic acid analogs, peptides and proteins including molecules derivatized by methylation, glycosylation, phosphorylation, acetylation, myristoylation, prenylation, palmitation, amidation, and/or addition of glycosylphosphatidyl inositol.

Synthesis of Compounds

The compounds of the present invention can be prepared readily according to the following schemes and specific examples, or modifications thereof, using generally available starting materials, reagents and conventional synthesis procedures. In these reactions, it is possible to make use of variants which are themselves known to those of ordinary skill in this art but not mentioned in greater detail. The general procedure for making the compounds claimed in this invention can be readily understood and appreciated by one skilled in the art from viewing the following Schemes and without undue experimentation.

In some embodiments, the polymer structure and composition as well as the HLB can be methodically controlled, which may allow for compounds to be prepared under reproducible conditions. This methodology is an improvement to traditional polymer syntheses as traditional synthetic methods typically generate a Gaussian distribution of molecular weights (Mw) compounds that can differ from batch to batch.

In some embodiments, the compounds of Formula I and Formula II range in molecular weight from about 1,000 to 30,000. In further embodiments, the molecular weight for the compounds of Formula I and Formula II is from about 1,000 to 20,000 Da. The HLB of the polymers may range from ca. 3-30, depending on their composition. In an embodiment, the HLB is from ca. 10-25. The charge density is dependent on the size and structure of the amines and polyamines used to produce compounds of Formula I and Formula II. As understood by one of skill in the art, the molecular weight, HLB, and positive charges depend on the composition of polymers provided by the reaction conditions such as the feed ratio, reaction temperature, reaction time, etc. Generally, in embodiments of compounds of Formula I, the molecular size may be from 1,000 to 15,000. The positive charges may be increased if the molecule is substituted by two cationic segments. The HLB may be varied according to properties of the amphiphilic substitution and cationic segments. Generally, the HLB will be low when the PPI or other dendrimers function as the cationic substitute against PEI or other small amines. In embodiments of compounds of Formula II, the molecular size may be larger and up to 20,000 compared to those of Formula I, and the HLB or positive charges abide by the same principles as discussed in relation to Formula I.

In particular embodiments, the present invention provides compositions comprising, consisting essentially of or consisting of amphiphilic cationic polymers. In some embodiments, the amphiphilic cationic polymers have an intermediate size and HLB. In other embodiments, the amphiphilic cationic polymers include one or two biocompatible amphiphilic substitutions and one or two organic cations. The biocompatible amphiphile can be, for example, a Jeffamine, a poloxamer, a poloxamine, a polycaprolactone diol, a polycaprolactone polytetrahydrofuran block copolymer, a polysorbate polymer (e.g., a Tween series polymer), or a Triton polymer. The organic cation can be, for example, an amine, such as polyethylenimine (PEI), polypropylenimine (PPI), a low molecular weight amine, a dendrimer, or a polypeptide (e.g., poly-L-arginine or poly-L-lysine). In some embodiments, compositions of the present invention further include a therapeutic or diagnostic agent. In certain embodiments, the therapeutic or diagnostic agent is a nucleic acid, such as an oligonucleotide or a transgene. In other embodiments, the therapeutic or diagnostic agent is a protein or a bulky, non-hydrophobic molecule. The therapeutic agent can be useful, for example, for treatment of a genetic disease, such as muscular dystrophy, and in particular, Duchenne muscular dystrophy.

In this application, cyanuric chloride is used as the starting material to create triazine cored amphiphilic polymers for therapeutic delivery. Cyanuric chloride is used as the starting material as the chlorides can be readily displacement by various nucleophiles. The use of cyanuric chloride allows for the preparation of mono-, di-, and trisubstituted 1,3,5-triazine derivatives under controlled reaction conditions and feed ratios.

The synthesis of some triazines according to embodiments of the present invention can be conducted as described in Scheme 1.

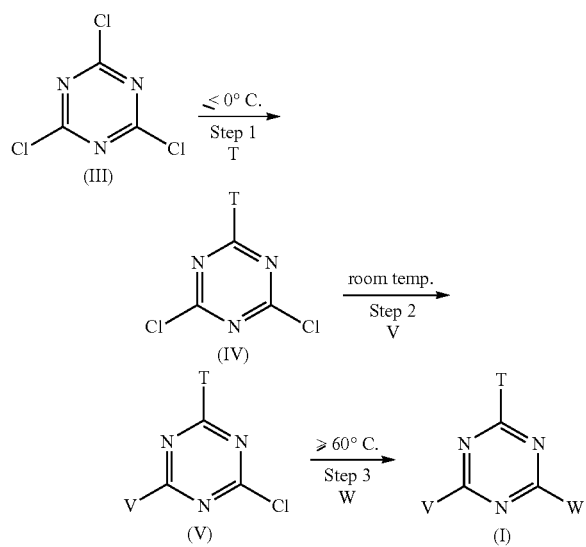

Scheme 1 illustrates a general strategy for the preparation of compounds of general Formula (I) of the present invention. As will be readily appreciated by those skilled in the art, there are many variations of the routes shown in Scheme 1 that may be useful for synthesizing compounds of general Formula (I).

In step 1, cyanuric chloride (Compound III) is diluted with an organic solvent and the reaction temperature is maintained at about or below zero degrees Celsius. The next step is to react with a nucleophile T to generate a compound of general Formula (IV).

In step 2, a compound of general Formula (IV) is diluted with an organic solvent and the reaction temperature is maintained at about ambient temperature. The reaction is next diluted with a nucleophile V, to generate a compound of general Formula (V).

In step 3, a compound of general Formula (V) is diluted with an organic solvent and the reaction temperature is maintained at about or above about 60° C. The reaction is next diluted with a nucleophile W to generate a compound of general Formula (I). Methodologies for the synthesis of compounds of the general Formula (I) may be found in the following publication: Tetrahedron, Vol. 62, 9507-9522, 2006. This reference is included as an illustrative example only and should not be interpreted as exhaustive or limiting of the invention in any way.

The synthesis of some triazines according to embodiments of the present invention can be conducted as described in Scheme 2.

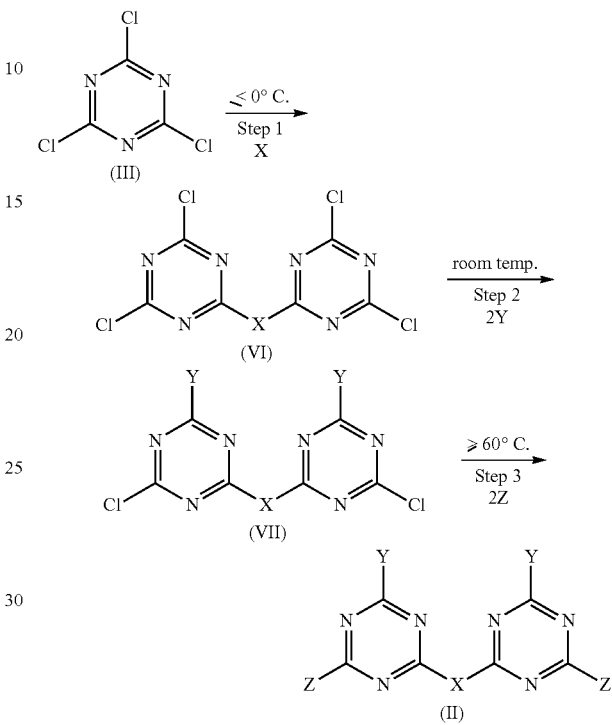

Scheme 2 illustrates a general strategy for the preparation of compounds of general Formula (II) of the present invention. As will be readily appreciated by those skilled in the art, there are many variations of the routes shown in Scheme 1 that may be useful for synthesizing compounds of general Formula (II).

In step 1, cyanuric chloride (Compound III) is diluted with an organic solvent and the reaction temperature is maintained at about or below about 0° C. The reaction is next diluted with a dinucleophile X to generate a compound of general Formula (VI).

X represents a linker moiety. In general, the linker is not biodegradeable. In some embodiments, the linker is or is derived from a diol, alkyl, dithiol, diamine or polyamine. In some embodiments, X is a diamine or polyamine. In other embodiments, X is a diol. In further embodiments, the diols are lipoloxamers and poloxamers useful as biocompatible amphiphiles in an amphiphilic cation polymer of the invention. The lipoloxamers and poloxamers can have a formula selected from the group consisting of:

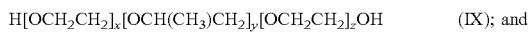

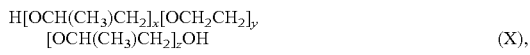

wherein x, y, and z each have a value from about 5 to about 80. In some embodiments, x, y, and z each have a value from about 10 to about 65, about 15 to about 55, or about 20 to about 50. Persons skilled in the art will understand that Formulas (VIII) through (X) are oversimplified in that, in practice, the orientation of the isopropylene radicals will be random.

In step 2, a compound of general Formula (VI) is diluted with an organic solvent and the reaction temperature is maintained at about 25° C. The reaction is next diluted with a two mole excess of nucleophile Y, to generate a compound of general Formula (VII).

In step 3, a compound of general Formula (VII) is diluted with an organic solvent and the reaction temperature is maintained at about or above about 60° C. The reaction is next diluted with a two mole excess of nucleophile Z to generate a compound of general Formula (II).

Figure 2:
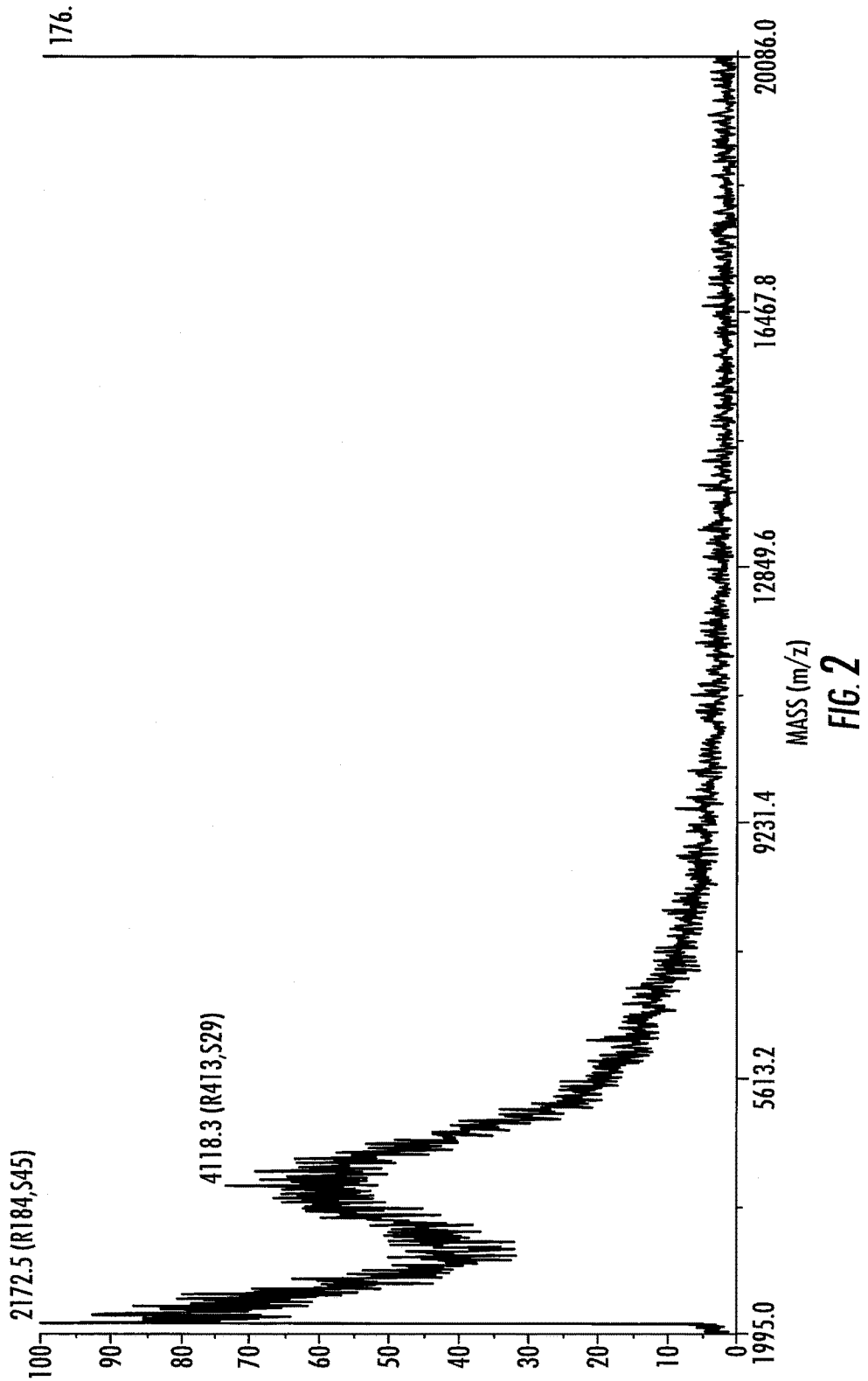
FIG. 2 depicts the mass spectrum of $1A_41B_3$.
Figure 3:
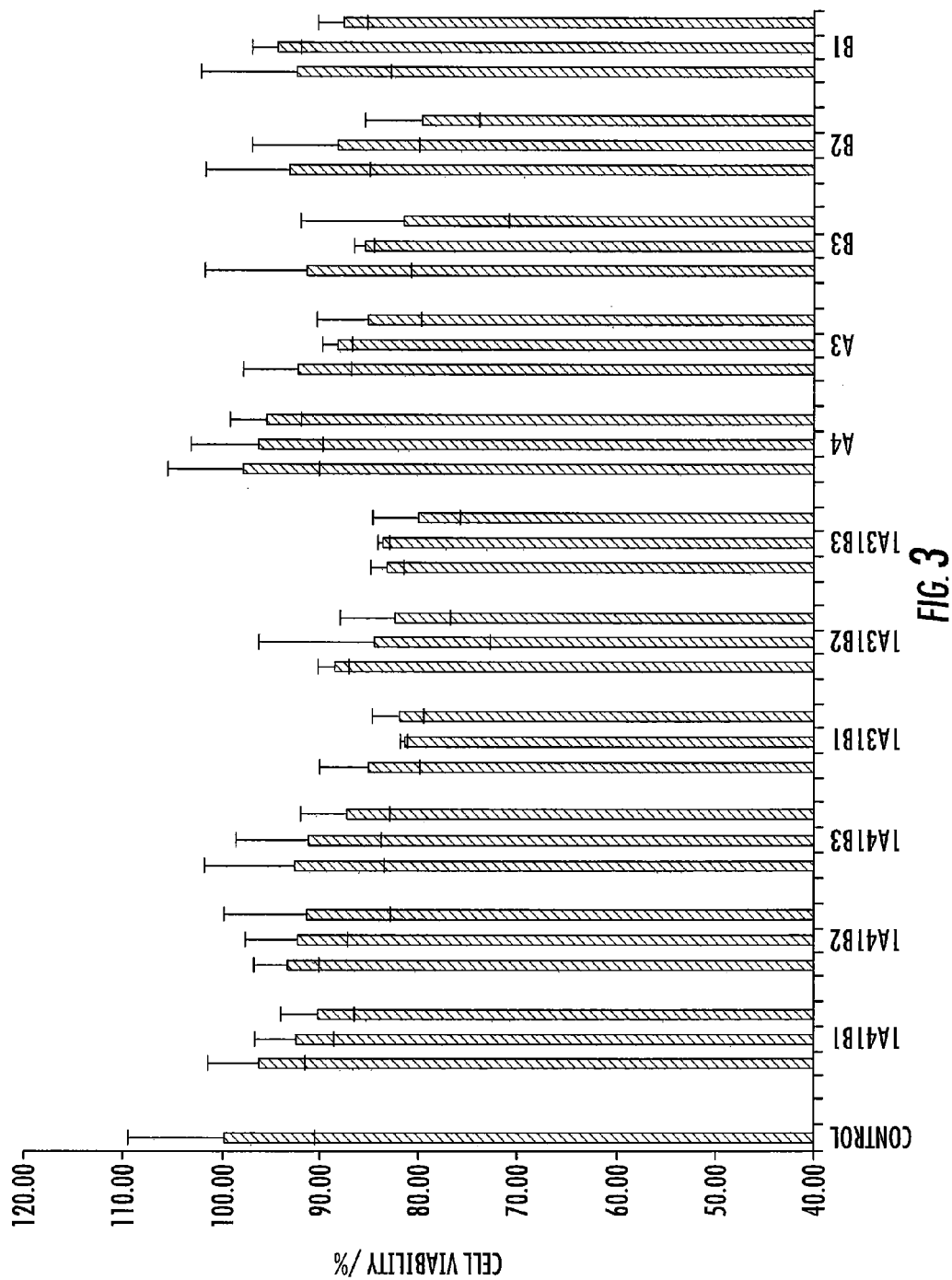
FIG. 3 demonstrates cell viability in the C2C12 myoblast cell line at the doses of 5, 10, and 25 μg/mL, respectively, for the polymers designated on the x-axis.

Simple modifications of these routes may be employed. Application of well-precedented methodologies and the use of starting materials and reagents other than those described in the foregoing schemes may be used to provide other compounds of interest, such as those detailed in Examples 1-11 as within the purview of those skilled in the art. Further, a more detailed description of the figures presents further guidance regarding the synthesis and use of the compounds of the present invention. FIG. 1 illustrates a $^1$H NMR spectrum obtained for the triazine $1A_4 1B_2$ in $D_2O$ obtained on a JEOL ECA-500 NMR. FIG. 2 illustrates the mass spectrum for the triazine derivative $1A_4 1B_3$. FIG. 3 illustrates the cell viability percentage for C2C12 cells incubated with the triazine derivatives 1A41B1, 1A41B2, 1A41B3, 1A31B1, 1A31B2, and 1A31B3 along with the synthons A4, A3, B3, B2 and B1. The cells were incubated with the corresponding compounds at concentrations of 5, 10, and 25 μg/mL. As shown in FIG. 3, the tested compounds were not cytotoxic to C2C12 cells at the illustrated concentrations.

Figure 4:
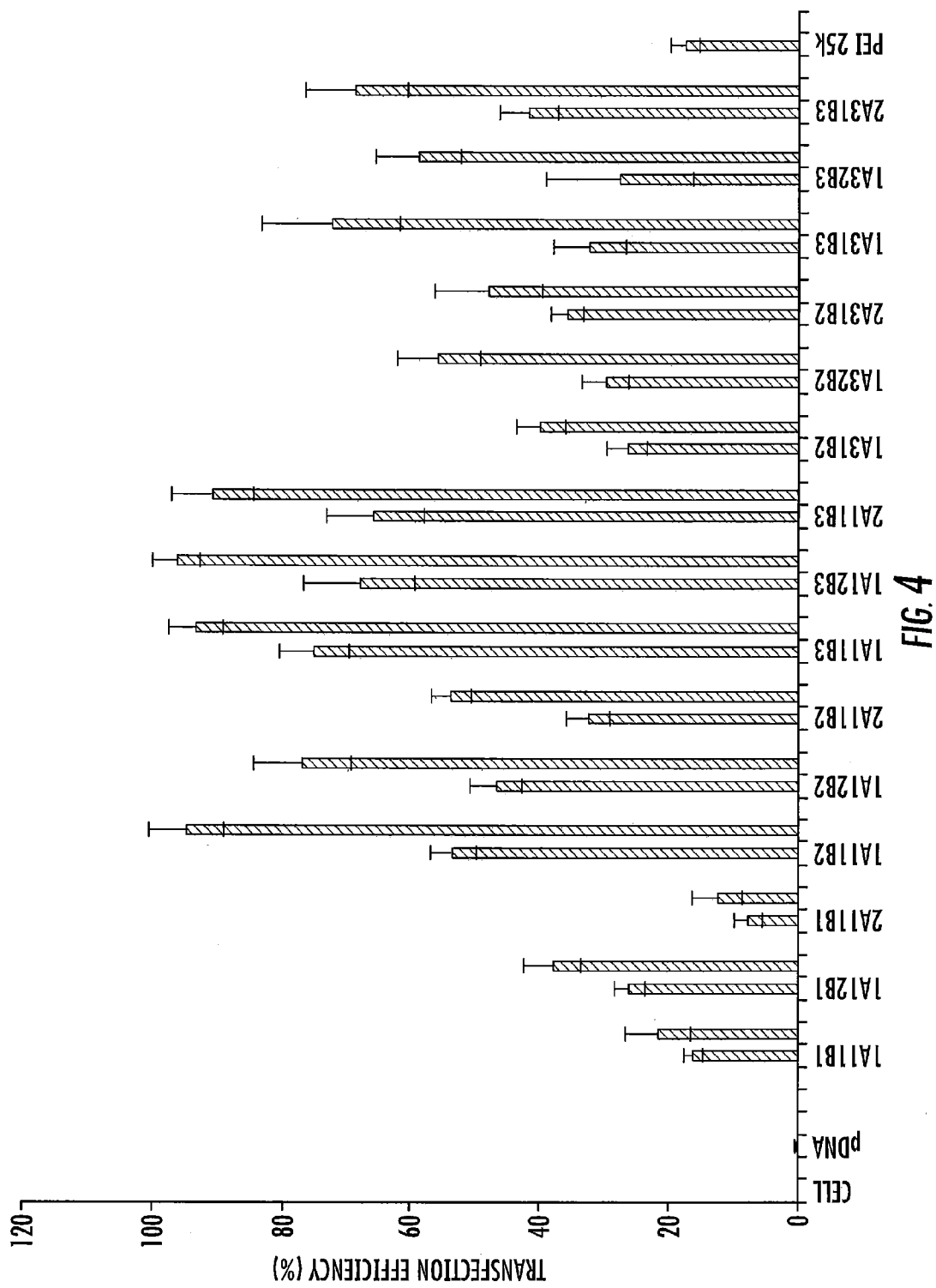
FIG. 4 demonstrates the in vitro transfection efficiency of polymer/pDNA complexes by FACS analysis in the CHO cell line at weight ratios of polymer/pDNA=5, 10, respectively. Transfections were performed at a dose of 1 μg pDNA.

FIG. 4 shows the in vitro transfection efficiency for polymer/pDNA complexes by FACS analysis in CHO cells with the weight ratios of polymer/pDNA being 5 and 10. The transfections were performed at a dose of 1 μg pDNA.

Figure 5:
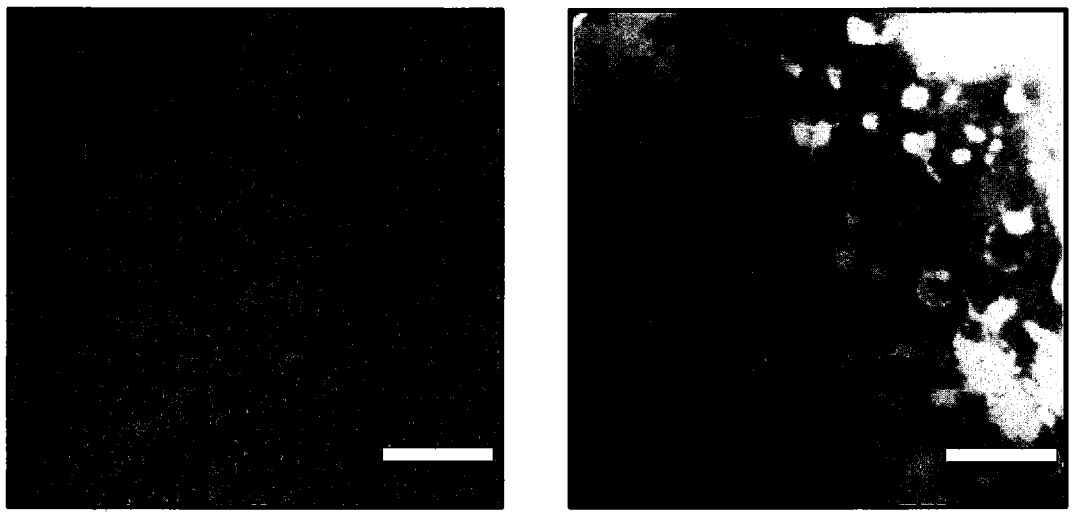
FIG. 5 presents negative stain transmission electron microscopy (TEM) images of Polymer (1A31B2)/pDNA condensates (left), and pDNA alone (right) (Scale bar: 200 nm).

As schematically illustrated in FIG. 5, the Figure on the left shows the negative stain transmission electron microscopy (TEM) images of the polymer 1A31B2/pDNA condensates in comparison to the TEM images of pDNA in the figure on the right. The scale bar has a length of 200 nm.

Figure 6:
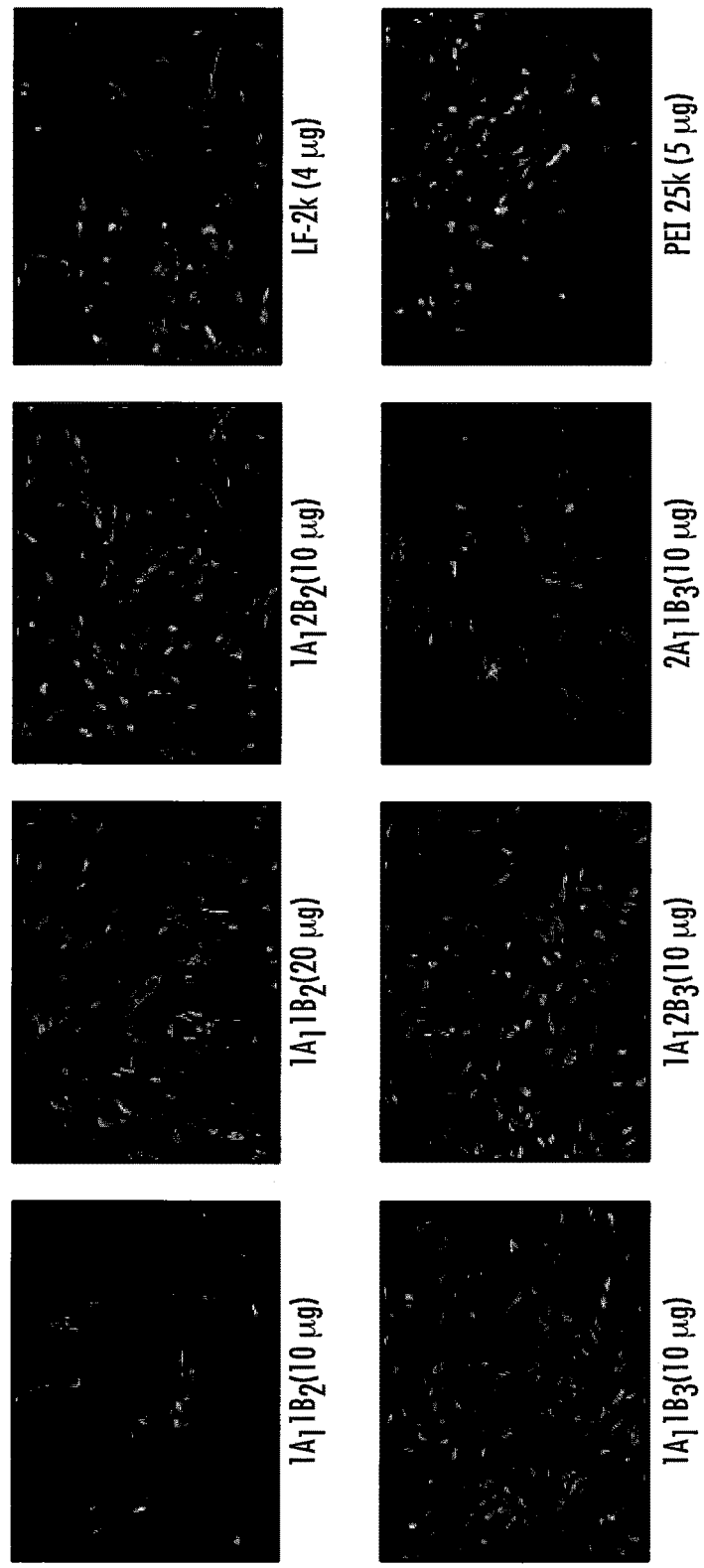
FIG. 6 shows green fluorescent protein (GFP) expression in C2C12 cell line with polymer formulated with 1 μg pDNA of GFP expression vector in 10% FBS-DMEM. The cells were incubated under 37° C. and 10% $CO_2$. The images were taken 48 hours after transfection.

FIG. 6 illustrates GFP expression in C2C12 cell line with 1 μg pDNA of GFP expression vector and 10% FBS/DMEM formulation. The cells were incubated under 37° C. and 10% $CO_2$. The images were taken 48 hr after transfection.

Figure 7:
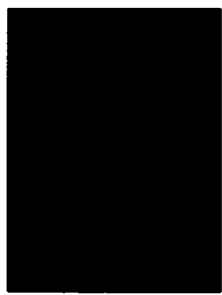
FIG. 7 shows GFP induction with PMOE23 targeting human dystrophin exon 23 in the GFP/E23 C2C12 reporter cells. The insertion of human dystrophin exon 23 disrupts the GFP reading frame. The expression of GFP represents the skipping of exon 23, which restores GFP reading frame. All samples were treated with 5 μg PMO in 500 μL medium. The results provide dose-dependent expression of GFP with the polymer 1A41B2 (5, 10, or 20 μg) in combination with PMO (5 μg) in 10% FBS-DMEM. Endoporter (5 μg) formulated PMO was used as a positive comparison.
Figure 7:
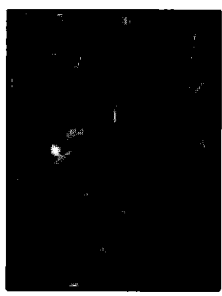
Figure 7:
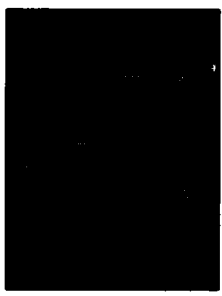
Figure 7:
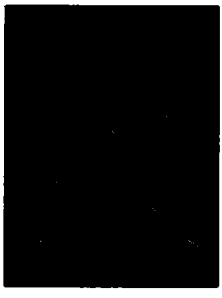
Figure 7:
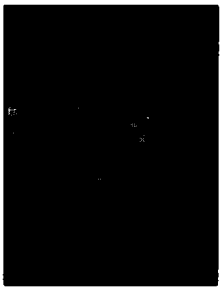

FIG. 7 illustrates GFP induction with PMO E23 targeting human dystrophin exon 23 in the GFP/E23 C2C12 myoblast reporter cells. The insertion of human dystrophin exon 23 disrupts the GFP reading frame. The expression of GFP represents the skipping of exon 23, which restores GFP reading frame. All samples were treated with 5 μg PMO in 500 μL medium. The results provide dose-dependent expression of GFP with the polymer 1A41B2 (5, 10, or 20 μg) in combination with PMO (5 μg) in saline.

Figure 8:
FIG. 8 presents GFP induction with PMOE23 targeting human dystrophin exon 23 in GFP/E23 C2C12 myoblast reporter cells. The three polymers have the same PEI 1.2 k, but with a different hydrophilic-lipophilic balance (HLB).

FIG. 8: GFP induction with PMO E23 targeting human dystrophin exon 23 in GFP/E23 C2C12 myoblast reporter cells. The three polymers have the same PEI 1.2 k, but with a different HLB.

As illustrated in FIGS. 6, 7, and 8, high transfection efficiency in vitro: balanced HLB together with optimal size of polyamine provides highest potential for transfection efficiency (TE) with lowest toxicity when compared with PEI 25 k for pDNA or Endoporter for antisense oligomer PMO delivery.

Figure 9:
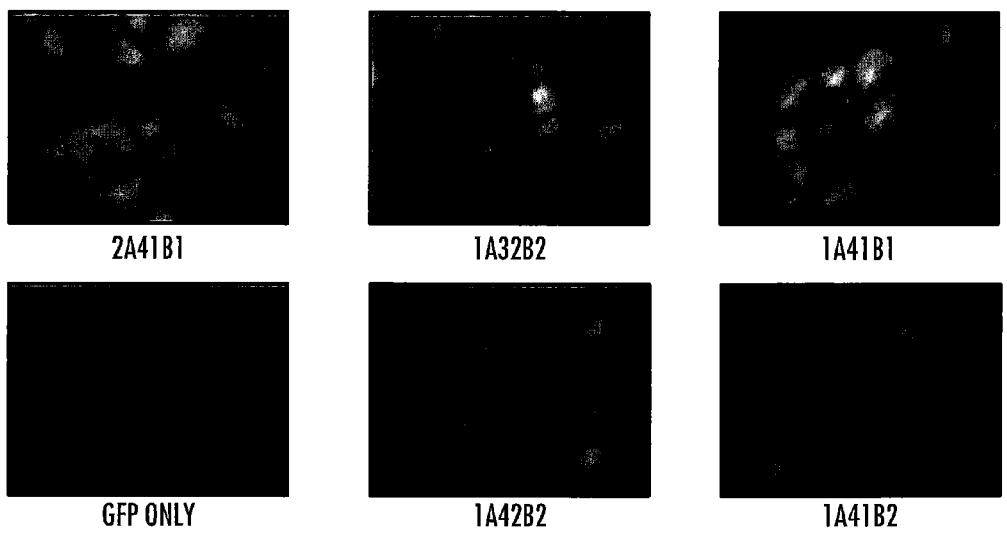
FIG. 9 shows expression of GFP in muscles of mdx mice (age 4-6 weeks) 5 days after i.m. injection of the polymer formulated pDNA in saline.

FIG. 9 shows expression of GFP in muscles of mdx mice (age 4-6 weeks) 5 days after i.m. injection of polymer formulated pDNA in saline.

Figure 10:
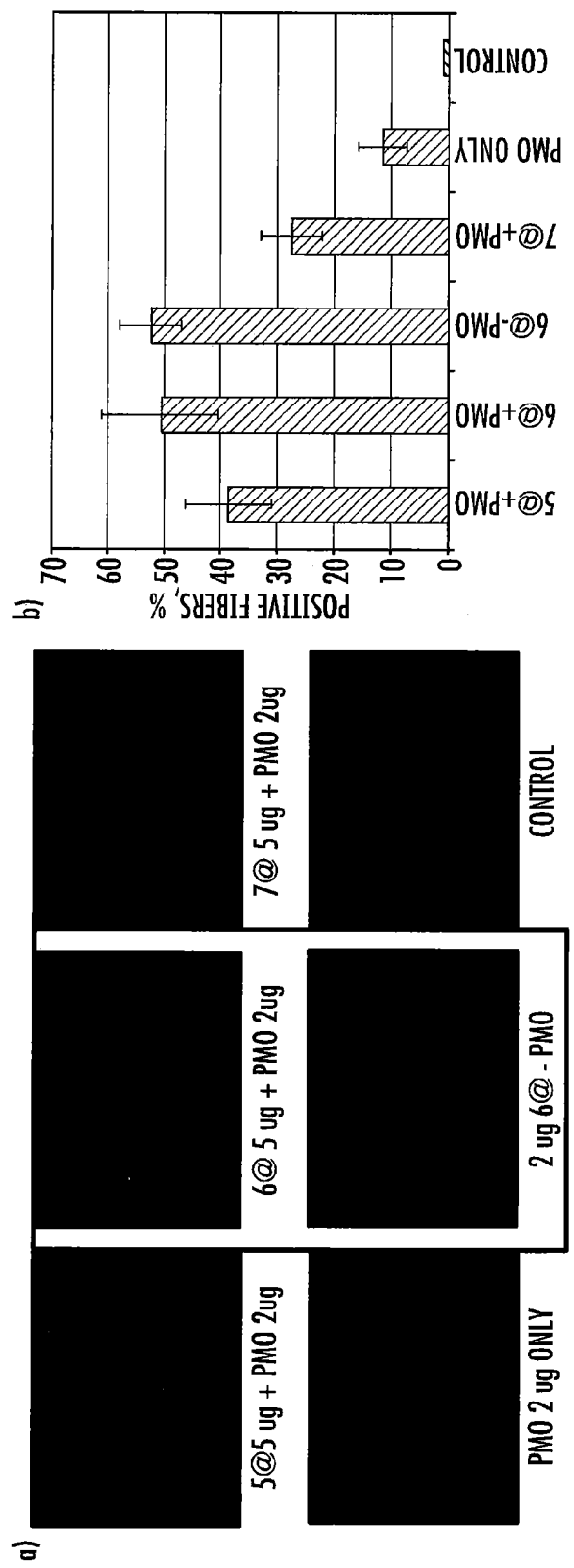
FIG. 10 presents the restoration of dytrophin in TA muscles of mdx mice (age 4-5 weeks) 2 weeks after i.m. injection of polymer formulated PMO targeting mouse dystropin exon 23. a) Dystrophin expression was detected by immunohistochemistry with rabbit polyclonal antibody P7 against dystrophin. Blue nuclear staining with DAPI. PMOE23 (2 μg) was mixed with each polymer (5 μg or 2 μg) in 40 μL saline. b) Statistical analysis of dystrophin positive fibers. Y bar indicates the % of muscle fibers expressing dystrophin. The remaining fibers are dystrophin negative.

FIG. 10 illustrates the restoration of dytrophin in TA muscles of mdx mice (age 4-5 weeks) 2 weeks after i.m. injection of polymer formulated PMO targeting mouse dystropin exon 23. a) Dystrophin expression was detected by immunohistochemistry with rabbit polyclonal antibody P7 against dystrophin. Blue nuclear staining with DAPI. PMO E23 (2 μg) was mixed with each polymer (5 μg or 2 μg) in 40 μL saline. b) Statistical analysis of dystrophin positive fibers. Y bar indicates the % of muscle fibers expressing dystrophin. The remaining fibers are dystrophin negative.

Figure 11:
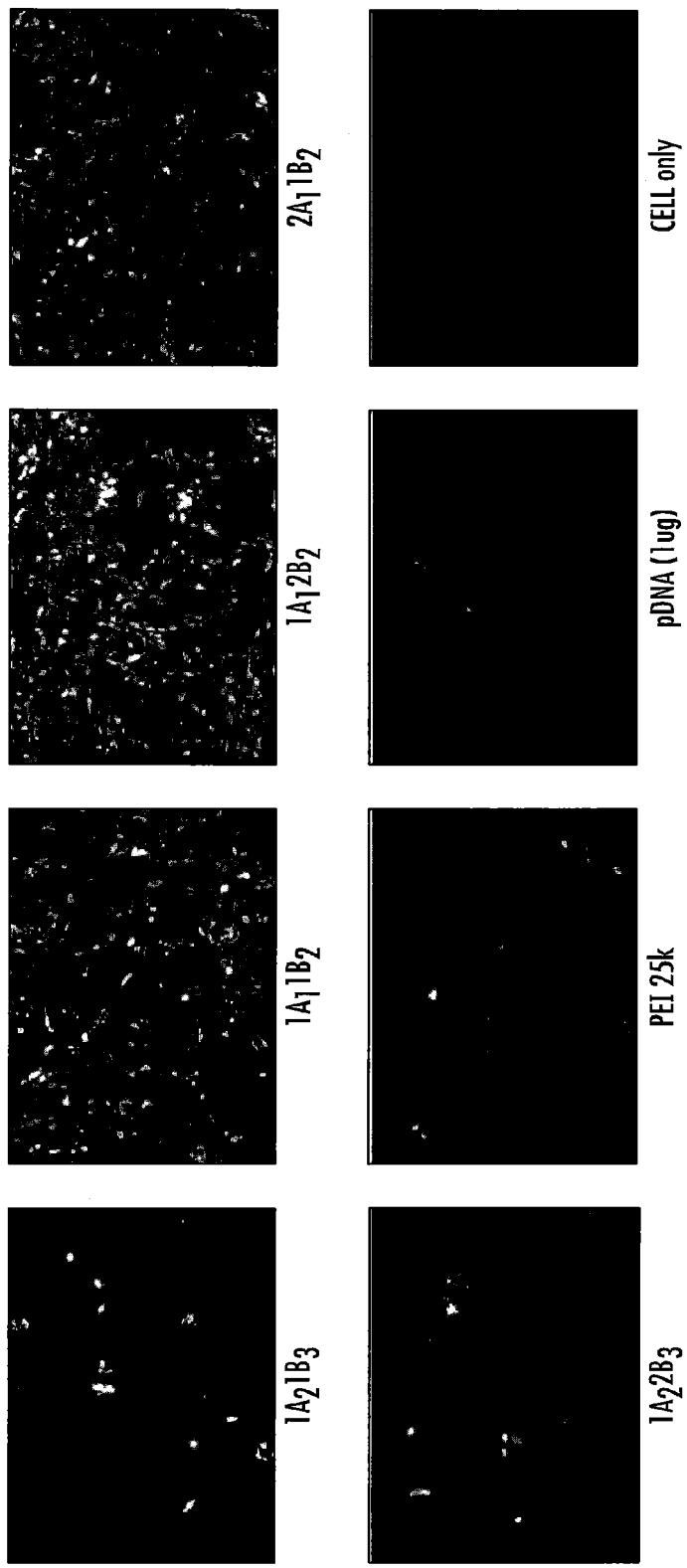
FIG. 11 depicts GFP expression of polymer-mediated pDNA delivery in LNCaP cells. Polymer (5 μg) and pDNA (1 μg) in 500 μl 10% FBS medium.

FIG. 11 shows expression of GFP in LNCaP human prostatic carcinoma cells transfected using the polymer-mediated pDNA delivery. Transfections were performed using 5 μg polymer, 1 μg pDNA in 500 μl medium. Polymer-mediated pDNA delivery was also examined in MCF-7 breast carcinoma cells. The transfection efficiency observed in MCF-7 cells was similar to the transfection efficiency observed for LNCaP cells (data not shown).

Figure 12:
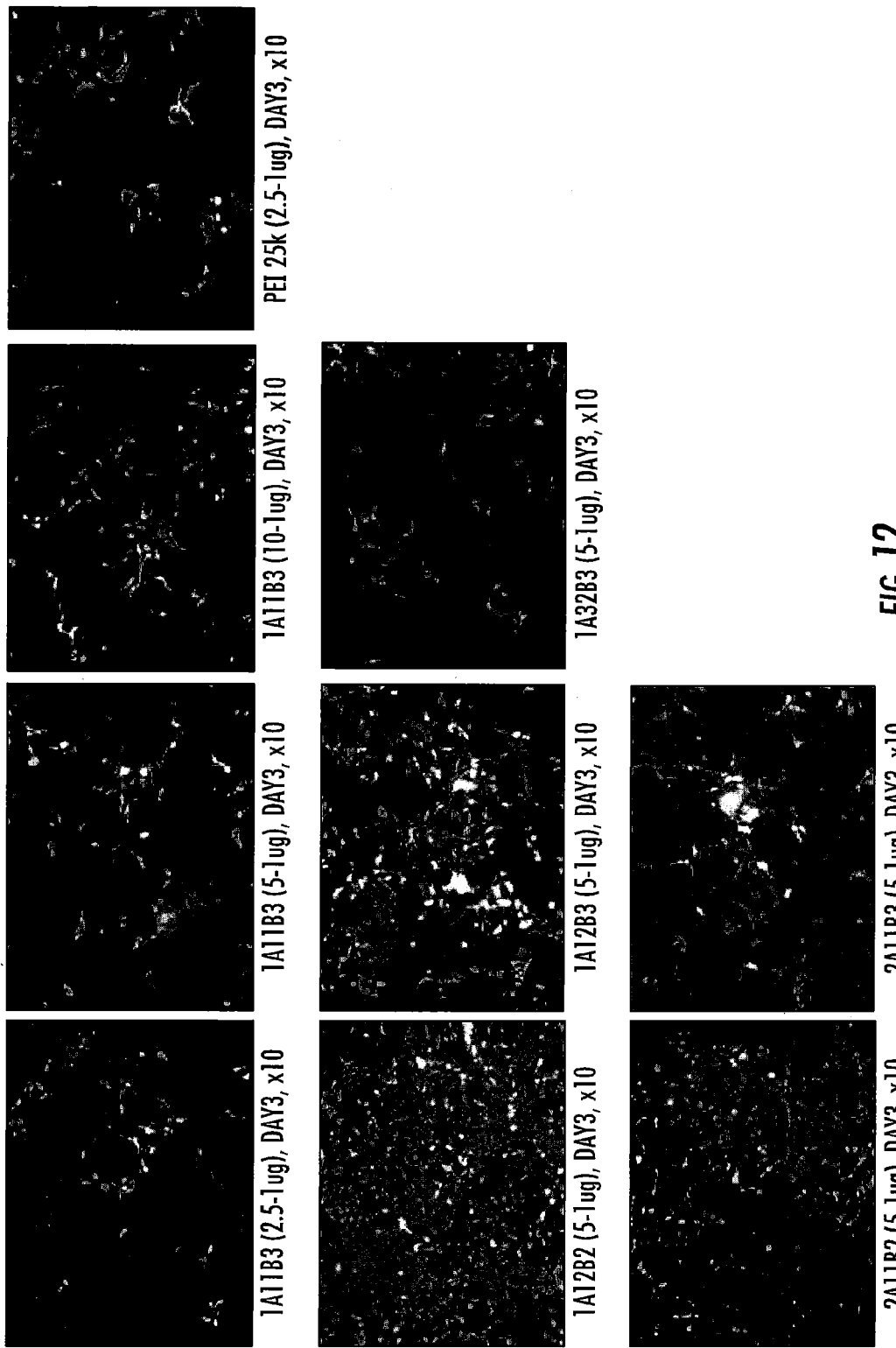
FIG. 12 depicts GFP expression of polymer-mediated pDNA delivery in HEK 293 cells. Polymer (2.5, 5, 10 μg) and pDNA (1 μg) in 500 uL 10% FBS medium.

FIG. 12 shows expression of GFP in HEK 293 cells transfected using polymer-mediated pDNA delivery using 2.5, 5 and 10 μg polymer, 1 μg pDNA in 500 μl medium. The results indicated that: 1) the transfection efficiency of pDNA delivery was improved using the polymer-mediated system of the invention when compared with PEI 25 k at the tested dosages; 2) the transfection efficiency was related to the hydrophilic-lipophilic balance (HLB) in vitro. More effective delivery was observed with more hydrophobic polymer compositions; and 3) the delivery efficiency was not particularly proportional to the increase in the amount of polymer, for example, as exhibited by transfection using differing amounts of 1A11B3 in HEK 293 cells (see, FIG. 12). These results show little significant difference in GFP expression, indicating a low toxicity of the polymer in vitro.

Further exemplary structures include, but are not limited to, the following:

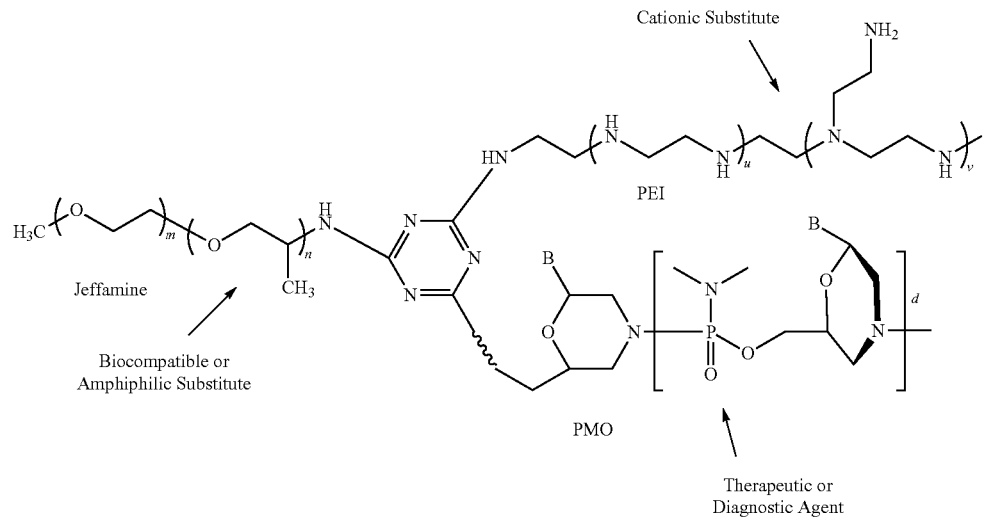

The biocompatible amphiphile can also be, for example, a poloxamer, a poloxamine, a polycaprolactone diol, a polycaprolactone polytetrahydrofuran block copolymer, a polysorbate polymer (e.g., a Tween series polymer), or a Triton polymer. The organic cation can also be, for example, an amine, such as polypropylenimine (PPI), a low molecular weight amine, a dendrimer, or a polypeptide (e.g., poly-L-arginine or poly-L-lysine). In certain embodiments, the therapeutic or diagnostic agent is a nucleic acid, proteins, and other chemical compounds (e.g., pharmaceutical drugs, peptide, and diagnostic imaging agents).

Pharmaceutical Formulations

The compounds of Formula I and II as described herein may be formulated for administration in a pharmaceutical carrier in accordance with known techniques. See, e.g., Remington, *The Science and Practice of Pharmacy* ($9^{th}$ Ed. 1995). In particular, compounds of Formula I and II of the present invention can be combined with a pharmaceutically acceptable carrier to provide pharmaceutical formulations thereof. The particular choice of carrier and formulation will depend upon the particular route of administration for which the composition is intended.

The compositions of the present invention may be suitable for parenteral, oral, inhalation spray, topical, rectal, nasal, buccal, vaginal or implanted reservoir administration, etc. The term "parenteral" as used herein includes subcutaneous, intradermal, intravenous, intramuscular, intra-articular, intra-synovial, intrasternal, intrathecal, intrahepatic, intralesional and intracranial injection or infusion techniques. In particular embodiments, the compounds of Formula I and II are administered intravenously, orally, intranasally, subcutaneously, intradermally, intramucosally or via intramuscular administration.

For oral administration, the active compounds may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Formulations suitable for buccal (sub-lingual) administration include lozenges comprising the active compound in a flavored base, usually sucrose and *acacia* or tragacanth; and pastilles comprising the compound in an inert base such as gelatin and glycerin or sucrose and *acacia*.

Formulations of the present invention suitable for parenteral administration comprise sterile aqueous and non-aqueous injection solutions of the active compound(s), which preparations are preferably isotonic with the blood of the intended recipient. These preparations may contain anti-oxidants, buffers, bacteriostats and solutes which render the formulation isotonic with the blood of the intended recipient. Aqueous and non-aqueous sterile suspensions may include suspending agents and thickening agents.

Sterile injectable forms of the compositions of this invention may be aqueous or oleaginous suspensions. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound(s) of Formula I or II, or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, emulsion, lotion, paste, gel, spray, foam, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidylcholines, and lecithin.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multi-dose use. Of course, as indicated, the pharmaceutical compositions of the present invention may be lyophilized using techniques well known in the art.

The amount of the compounds of the present invention that may be combined with the carrier materials to produce a composition in a single dosage form will vary depending upon the subject treated and the particular route of administration. In particular embodiments, the compositions should be formulated so that a dosage of between 0.01-100 mg/kg body weight/day of the active agent can be administered to a patient receiving these compositions. In certain embodiments, the compositions of the present invention provide a dosage of between 0.01 mg and 50 mg is provided. In other embodiments, a dosage of between 0.1 and 25 mg or between 5 mg and 40 mg is provided.

Therapeutic agents suitable for inclusion in the compositions of the invention include nucleic acids, proteins, and other chemical compounds (e.g., pharmaceutical drugs). In certain embodiments, the therapeutic agent is a nucleic acid. The nucleic acid can be DNA, RNA, or a modified nucleic acid, such as a peptide nucleic acid (PNA), Bridged nucleic acid (BNA) or a nucleic acid comprising 2'-O-methyl phosphorothioate (2'-OMePs), phosphorodiamidate morpholino oligonucleotides (PMO), Accordingly, the nucleic acid can be derivatized by methylation, glycosylation, phosphorylation, acetylation, myristoylation, prenylation, palmitation, amidation, and/or addition of glycosylphosphatidyl inositol. In some embodiments, the nucleic acid can comprise an entire gene or cDNA, or a fragment thereof, such as a promoter fragment (e.g., an oligonucleotide decoy sequence comprising one or more transcription factor binding sites and/or an enhancer sequence), an intron sequence, an intron-exon junction sequence, a coding sequence, an antisense sequence, etc. The nucleic acid can be single or double stranded. Certain nucleic acids include an open reading frame encoding a functional protein. Other nucleic acids include antisense oligonucleotides or siRNAs that induces gene silencing or exon skipping. Still other nucleic acids include a double-stranded oligonucleotide decoy sequence capable of influencing the transcription of a target gene.

In other embodiments, the therapeutic agent is a polypeptide (e.g., a protein). The polypeptide can be, e.g., a vaccine, an antibody, a transcription factor (e.g., a transcription factor responsive to extracellular signaling events, such as a Notch receptor intracellular domain fragment), a cytoplasmic protein (e.g., involved in signal transduction, such as a kinase or adaptor protein that functions by binding to phosphorylated protein epitopes), or a dominant-negative protein mutant (e.g., that interferes with normal signal transduction). The polypeptide can also be, e.g., a growth factor or protein hormone.

In still other embodiments, the therapeutic agent is a chemical compound. The chemical compound can be, for example, an antibiotic; antiviral agent; analgesic or combination of analgesics; anorexic; antihelminthic; antiarthritic; antiasthmatic agent; anticonvulsant; antidepressant; antidiabetic agent; antidiarrheal; antihistamine; antiinflammatory agent; antimigraine preparation; antinauseant; antineoplastic; antiparkinsonism drug; antipruritic; antipsychotic; antipyretic; antispasmodic; anticholinergic; sympathomimetic; xanthine derivative; cardiovascular preparation, such as a potassium or calcium channel blocker, beta-blocker, alpha-blocker, or antiarrhythmic; antihypertensive; diuretic or antidiuretic; vasodilator, including general, coronary, peripheral or cerebral; central nervous system stimulant; vasoconstrictor; cough and/or cold preparation, including a decongestant; hormone, such as estradiol or other steroid, including a corticosteroid; hypnotic; immunosuppressive; muscle relaxant; parasympatholytic; psychostimulant; sedative; or tranquilizer. By the methods of the present invention, drugs in all forms, e.g., ionized, nonionized, free base, acid addition salt, and the like may be delivered, as can drugs of either high or low molecular weight.

Diagnostic agents suitable for inclusion in the compositions of the invention include any nucleic acid, polypeptide or chemical compound useful for diagnostic methods, including, for example, fluorescent, radioactive, or radio-opaque dye. After compositions (e.g., pharmaceutical compositions) comprising an amphiphilic cationic polymer of the invention combined with a diagnostic agent have been administered to an organism, the polymer and/or diagnostic agent can be tracked using well-known techniques such as, for example, but not limited to, positron emission tomography (PET), magnetic resonance imaging (MRI), computed tomography (CT), single-photon emission computerized tomography (SPECT), etc. In yet other embodiments, diagnostic methods include histopathological and immunohistopathological (IHC) methods, for example, but not limited to radioimmunoassays (RIA), fluorescence in situ hybridization (FISH) and flow cytometry. In still other embodiments, diagnostic methods include, in vitro diagnostic assays, for example, but not limited to, enzyme-linked immunoabsorbent assays (ELISA), polymerase chain reaction (PCR), examples of which include, but are not limited to, end-point PCR, real-time PCR (RT-PCR) and digital PCR, and DNA/

RNA sequencing, examples of which include, but are not limited to, next-gene sequencing and RNA-seq, and mass spectroscopy (MS).

In an attempt to enhance the action (e.g., therapeutic effect) of the compound of the present invention and/or decrease the amount of the compounds of the present invention to be used, and the like, as well as prevent or treat complications and improve prognosis, for example, the compounds of the present invention can be used in combination with a concomitant drug. Examples of such concomitant drug include an "agent for treating diabetes", "therapeutic drug for diabetic complications", "anti-obesity agent", "therapeutic drug for hypertension", "therapeutic drug for hyperlipidemia", "antiarteriosclerotic drug", "antithrombotic", "diuretic", "therapeutic drug for arthritis", "antianxiety drug", "antidepressant", "psychoneurotic agent", "sleep-inducing drug" and the like. These concomitant drugs may be low-molecular-weight compounds, or high-molecular-weight proteins, polypeptides, antibodies, vaccines or the like. In addition, two or more kinds of these concomitant drugs may be used in combination at an appropriate ratio.

Examples of the above-mentioned "agent for treating diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compound described in WO2007/013694, WO2007/018314, WO2008/093639 or WO2008/099794), a-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), 133 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37) NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF2 1, FGF analogue and the like.

Examples of the above-mentioned "therapeutic drug for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxyl)propyl]oxazole), the compounds described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-norepinephrine reuptake inhibitors (e.g., duloxetine), sodium channel inhibitors (e.g., lacosamide), active oxygen scavengers (e.g., thioctic acid), cerebral vasodilators (e.g., tiapuride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide γ antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like-peptide-1 (GLP-1) preparations (e.g., animal GLP-1 preparation extracted from pancreas of bovine and swine; human GLP-1 preparations genetically synthesized using *Escherichia coli*, yeast; fragment or derivative of GLP-1 (e.g., exenatide, liraglutide)), amylin preparations (e.g., pramlintide, AC-2307), neuropeptide γ agonists (e.g., PYY3-36, derivative of PYY3-36, obinepitide, TM-30339, TM-30335), oxyntomodulin preparations: FGF21 preparations (e.g., animal FGF21 preparation extracted from pancreas of bovine and swine; human FGF21 preparations genetically synthesized using *Escherichia coli*, yeast; fragment or derivative of FGF21)), anorexigenic agents (e.g., P-57) and the like.

Examples of the above-mentioned "therapeutic drug for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), β blockers (e.g., metoprolol, atenolol, propranolol, carvedilol, pindolol), clonidine and the like.

Examples of the above-mentioned "therapeutic drug for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compounds described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic drug" include acyl coenzyme A cholesterol acyltransferase (ACAT) inhibitors (e.g., K-604), LpPLA2 inhibitors (e.g., darapladib, rilapladib), 5-lipooxygenase-activating protein (FLAP) inhibitors (e.g., AM103, AM803 and the like), 5-lipooxygenase (5LO) inhibitors (e.g., VIA-2291), secreted phospholipase A2 (sPLA2) inhibitors (e.g., A-002), apolipoprotein A1 (apoA1) mimetic peptides (e.g., D4F), high density lipoprotein (HDL) preparations (e.g., CSL-111) and the like.

Examples of the above-mentioned "antithrombotic" include heparin (e.g., heparin sodium, heparin calcium, enoxaparin sodium, dalteparin sodium), warfarin (e.g., warfarin potassium), anti-thrombin drugs (e.g., aragatroban, dabigatran), FXa inhibitors (e.g., rivaroxaban, apixaban, edoxaban, YM150, the compounds described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichlormethiazide, hydrochlorothiazide, hydroflumethiazide, bentylhydrochlorothiazide, penflutiazide, polythiazide, methyclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic drug for arthritis" include ibuprofen and the like.

Examples of the above-mentioned "antianxiety drug" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, Japanese parsley purine), selective serotonin uptake inhibitors (e.g., fluoxetine, fluvoxamine, paroxetine, sertraline, escitalopram), serotonin noradrenaline uptake inhibitors (e.g., milnacipran, duloxetine, venlafaxine), trazodone, mirtazapine, moclobemide and the like.

Examples of the above-mentioned "psychoneurotic agent" include conventional antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing drug" include Ramelteon, GABAergic hypnotics brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

In another embodiment of the present invention, methods of facilitating delivery of a therapeutic or diagnostic agent into a cell are provided. The methods comprise, consist essentially of, or consist of contacting a cell with a composition comprising an amphiphilic cationic polymer of the present invention in combination with a therapeutic or diagnostic agent. In certain embodiments, the methods comprise, consist essentially of, or consist of contacting the cell with a pharmaceutical composition comprising an amphiphilic cationic polymer of the invention in combination with a therapeutic or diagnostic agent and a pharmaceutically acceptable carrier. In certain embodiments, the cell is contacted in vitro, such as in a cell culture dish. In other embodiments, the cell is contacted in vivo. In certain embodiments, the contacting step comprises, consists essentially of, or consists of administering the composition to an organism including the cell such that the composition is able to contact the cell. In certain embodiments, the composition is administered to the organism by injection. In other embodiments, the composition is administered to the organism orally, intranasally, rectally or topically. In still other embodiments, the composition is administered to the organism by providing the organism with the composition in a formulation suitable for injection, oral ingestion, or intranasal, rectal or topical application. In certain embodiments, the cell being contacted is from a primary culture of cells. In other embodiments, the cell being contacted is from an established cell line. In certain embodiments, the cell being contacted is selected from the group consisting of a muscle cell, a liver cell, an endothelial cell, a blood cell, an intestinal mucosal cell, a nasal mucosal cell, and a neuron. In particular embodiments, the cell being contacted is a muscle cell.

In another aspect, the invention provides methods of preventing or treating a condition in a subject. The methods comprise, consist essentially of, or consist of administering to the subject a composition comprising, consisting essentially of, or consisting of an amphiphilic cationic polymer of the invention optionally in combination with a therapeutic agent suitable for preventing or treating a disease in a subject. In some embodiments, the therapeutic agent is a nucleic acid. In other embodiments, the therapeutic agent is a protein or a bulky, non-hydrophobic molecule. In certain embodiments, the subject is an animal, such as a domesticated animal, a pet, a companion animal, a wild animal, a mammal or a bird. In some embodiments, the subject is a rodent, a human or a non-human primate. In some embodiments, the condition being prevented or treated is a genetic disease, such as muscular dystrophy. In particular embodiments, the genetic disease is Duchenne muscular dystrophy. In other embodiments, the condition being prevented or treated is an infection, such as a bacterial, fungal, or viral infection.

In particular embodiments, a subject of this invention is any subject in whom prevention and/or treatment of a metabolic or genetic disorder is needed or desired, as well as any subject prone to a metabolic or genetic disorder. In some embodiments, the subject is a human; however, a subject of this invention can include an animal subject, particularly mammalian subjects such as canines, felines, bovines, caprines, equines, ovines, porcines, rodents (e.g. rats and mice), lagomorphs, primates (including non-human primates), etc., including domesticated animals, companion animals and wild animals for veterinary medicine or treatment or pharmaceutical drug development purposes.

The subjects relevant to this invention may be male or female and may be any species of any race or ethnicity, including, but not limited to, Caucasian, African-American, African, Asian, Hispanic, Indian, etc., and combined backgrounds. The subjects may be of any age, including newborn, neonate, infant, child, adolescent, adult, and geriatric.

As used herein, a "genetic disease" or "genetic disorder" (wherein disease and disorder can be used interchangeably) refers to a condition caused by an abnormal genetic process. Examples of genetic disorders include, but are not limited to, cystic fibrosis, muscular dystrophies, color blindness, hemophilia, sickle-cell disease and cancer.

A particular genetic disease of interest is muscular dystrophy. The term "muscular dystrophy" (MD) encompasses a group of genetic diseases characterized by progressive weakness and degeneration of the skeletal muscles that control movement, including Duchenne MD, Becker MD, Facioscapulohumeral MD, and Myotonic MD.

Duchenne MD is the most common form of MD and primarily affects boys. Onset is typically between three and five years, and the disorder progresses rapidly. Some embodiments of the present invention relate to the prevention and treatment of Duchenne MD.

Cancers that have a genetic basis include cancers that are the result of genetically inherited mutations. Examples of such cancers include, but are not limited to, breast cancers, cancers which can be related to Li-Fraumeni syndrome, for example, childhood sarcomas, leukemias and brain cancers, cancers which can be related to Lynch syndrome, for example, colon cancers, bile duct cancers, brain cancers, endometrial cancers, kidney cancers, ovarian cancers, pancreatic cancers, small intestinal cancers, stomach cancers and ureter cancers, lung cancers, melanomas, prostate cancers, retinoblastomas, thyroid cancers and uterine cancers.

Moreover, cancers that have a genetic basis also include cancers that are the result of acquired mutations, for example, mutations resulting from diet, environment and/or lifestyle, or somatic mutations. Examples of such cancers include, but are not limited to, adrenal cancer, adrenal cortex cancer, bladder cancer, brain cancer, primary brain cancer, glioma, glioblastoma, breast cancer, cervical cancer, colon cancer (non-limiting examples include colorectal carcinomas such as colon adenocarcinoma and colon adenoma), endometrial cancer, epidermal cancer, esophageal cancer, gall bladder cancer, genitourinary cancer, head or neck cancer, kidney cancer, liver cancer, lung cancer (non-limiting examples include adenocarcinoma, small cell lung cancer and non-small cell lung cancer), lymphomas (non-limiting examples include B-cell lymphoma, T-cell lymphoma, Hodgkin's lymphoma, non-Hodgkin's lymphoma), melanoma, malignant melanoma, malignant carcinoid carcinoma, malignant pancreatic insulinoma, myeloma, multiple myeloma, ovarian cancer, pancreatic cancer (such as exocrine pancreatic carcinoma), prostate cancer, renal cell cancer, skin cancer, such as, in addition to others previously mentioned, squamous cell carcinoma, stomach cancer, testicular cancer, thyroid cancer, thyroid follicular cancer, Wilms' tumor, choriocarcinoma, mycosis fungoides, malignant hypercalcemia, cervical hyperplasia, leukemia, acute lymphocytic leukemia, chronic lymphocytic leukemia, hairy cell lymphoma, Burkett's lymphoma, acute myelogenous leukemia, chronic myelogenous leukemia, myelodysplastic syndrome, promyelocytic leukemia, acute granulocytic leukemia, chronic granulocytic leukemia, fibrosarcoma, rhabdomyosarcoma, astrocytoma, neuroblastoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, seminoma, teratocarcinoma, xenoderoma pigmentoum, keratoctanthoma and retinoblastoma.

A diagnosis of the genetic disease may be made by clinical observation and assessment and/or through diagnostic testing recognized as acceptable by those skilled in the art for determining the amount and/or duration of therapy.

The administration time of the aforementioned compounds and/or concomitant drug is not limited, and the compounds of the present invention and the optional concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The compounding ratio of the compound of the present invention to the concomitant drug can be appropriately selected depending on the administration subject, administration route, diseases and the like.

Embodiments of the present invention also provide kits including the elements necessary to carry out the processes described above. Such a kit may comprise a carrier being compartmentalized to receive in close confinement therein one or more containers, such as tubes or vials. One or more of the containers may contain a compound of the present invention. One or more containers may contain one or more enzymes or reagents to be utilized in desired reactions. These enzymes may be present by themselves or in admixtures, in lyophilized form or in appropriate buffers. The kit may contain all of the additional elements necessary to carry out techniques of the invention, such as buffers, control plasmid, oligonucleotides, extraction reagents, fixation agents, permeability agents, enzymes, pipettes, plates, nucleic acids, gel materials, transfer materials, autoradiography supplies, instructions and the like.

Having now described the invention, the same will be illustrated with reference to certain examples, which are included herein for illustration purposes only, and which are not intended to be limiting of the invention.

EXAMPLES

Some aspects of the present invention are described in more detail in the following non-limiting Examples. These are not intended to restrict the present invention, and may be modified within the range not deviating from the scope of this invention.

The "room temperature" in the following Examples and Experimental Examples means a temperature of about 15° C. to 30° C. For drying an organic layer, anhydrous magnesium sulfate or anhydrous sodium sulfate was employed. Unless otherwise specifically indicated, "%" means percent by weight.

Additional abbreviations used in the present specification mean the following: Ac=acetyl, Me=methyl, s=singlet, d=doublet, t=triplet, q=quartet, dd=double doublet, dt=double triplet, m=multiplet, br=broad, J=coupling constant, Hz=Hertz, $CDCl_3$=deuterated chloroform, DMA=dimethylacetamide, THF=tetrahydrofuran, NMP: 1-methyl-2-pyrrolidone, DMF=N,N-dimethylformamide, DMSO: dimethyl sulfoxide, $^1$H-NMR=proton nuclear magnetic resonance, MALDI-TOF Mass=mass spectrometry technology—Matrix Assisted Laser Desorption Ionization Time-of-Flight.

When the source of a simple precursor is unspecified, these compounds may be obtained from commercial suppliers of according to literature procedures.

Example 1

Reaction of Jeffamine A4 with Cyanic Chloride

A three-necked round-bottomed flask equipped with a magnetic stirring bar, nitrogen inlet-outlet lines, and a thermometer, was charged with cyanic chloride (1.5 mmol) and anhydrous tetrahydrofuran (20 mL). The reaction was cooled to an internal temperature below 4° C. under a nitrogen atmosphere. Jeffamine M-2070 (A4, 1.5 mmol) was added to the above solution, stirred for 5 minutes and followed by adding triethylamine (1.5 mmol). Stirring was continued overnight. The intermediate (1A4-C—$Cl_2$) was filtered, and concentrated.

Example 2

Reaction of 1A4-C—$Cl_2$ with PEI

1A4-C—$Cl_2$ (0.5 mmol), B2 (PEI 1.2 k, 0.6 mmol) and anhydrous N,N-dimethylformamide (10 mL) were combined and stirred at room temperature for 24 h. The mixture was diluted with deionized water (10 mL), dialyzed against water (membrane MWCO, 1k Da depends on the starting materials size), and the product (1A41B2) was lyophilized. Characterization by Nuclear Magnetic Resonance (JEOL ECA-500 NMR) and MALDI-TOF-Mass indicated the following: $^1$H NMR ($D_2O$): The signals at δ 1.1 ppm (methyl) and 3.2-3.7 (methylene and methyl) are from the Jeffamine moiety, and the signals at δ 2.4-2.7 ppm are from the PEI.

Example 3

Reaction of Jeffamine A4 (2×) with Cyanic Chloride (1×)

A three-necked round-bottomed flask equipped with a magnetic stirring bar, nitrogen inlet-outlet lines, and a thermometer, was charged with cyanic chloride (1.5 mmol) and anhydrous tetrahydrofuran (20 mL). The reaction was stirred at room temperature under a nitrogen atmosphere. The reaction was diluted with A4 (3 mmol), stirred for 5 minutes and further added triethylamine (3.0 mmol). Stirring was continued overnight. The intermediate (2A4-C—Cl) was filtered, and concentrated.

Example 4

Reaction of 2A4-C—Cl with PEI

Compound 2A4-C—$Cl_2$ (0.5 mmol) and PEI 1.2 k (B2, 0.6 mmol) in 10 mL anhydrous N,N-dimethylformamide (10 mL) were stirred at 60° C. for 8 h. The reaction was diluted with deionized water (10 mL), dialyzed against water (membrane MWCO, 1 k Da), and lyophilized, the product 2A41B2 was obtained and characterized.

Example 5

Reaction of 1A4-C—$Cl_2$ (1×) with PEI (3×)

Compound 1A4-C—$Cl_2$ (0.5 mmol) and PEI 1,2 k (1.5 mmol) in anhydrous N,N-dimethylformamide (10 mL) were stirred at 60° C. for 8 h. The reaction was diluted with deionized water (10 mL), dialyzed against deionized water (membrane MWCO, 1 k Da), and the product (1A42B2) was obtained by lyophilizing the aqueous solution.

Example 6

Complexation Study of Polymer/DNA

All polymer/DNA complexes were prepared immediately before use by gently vortexing a mixture of DNA and polymer solution at various polymer/DNA weight ratios. The complexes were incubated at room temperature for 30 minutes in 24 µL volume, then loaded onto 1% agarose gel with ethidium bromide (0.1 µg/mL) in tris-acetate (TAE) buffer (100V, 40 minutes). The gel was analyzed on a UV illuminator.

Example 7

Particle Size and Zeta Potential Measurement

Zeta Potential measurements of polymer/DNA complexes were performed at 25° C. using a Zetaplus Zeta Potential Analyzer (Brookhaven Instrument Co., NY) equipped with a 15 mV solid-state laser operated at a wavelength of 635 nm. Effective hydrodynamic diameter was measured by photon correlation spectroscopy using the same instrument at 25° C. with the angle of 90°. Polymer/pDNA complexes were prepared in 0.9% sodium chloride (AQUALITE@SYSYEM, Hospira, Inc., IL, USA).

Example 8

Transmission Electron Microscope (TEM)

The morphologies of the polymer/DNA complexes were analyzed using TEM (Phillips CM-10). The samples were prepared using negative staining with 1% phosphotungstic acid. Briefly, one drop of polymer/pDNA complex solution was placed on a formvar and carbon coated carbon grid (Electron Microscopy Sciences, Hatfield, Pa.) for 1 hour and the grid was blotted dry. Samples were then stained for 3 minutes and the grids were blotted dry. Samples were analyzed at 60 kV. Digital images were captured with a digital camera system from 4pi Analysis (Durham, N.C.).

Example 9

Cell Lines and Cell Culture

C2C12 myoblasts, Chinese Hamster Ovary (CHO), and C2C12E50 or C2C12E23 [the cell has a human dystrophin exon sequence 50 (hDysE50) or mouse dystrophin exon 23 (mDysE23) placed inside the coding sequence of a GFP gene under the control of an actin promoter. Upon specific antisense oligonucleotide delivery, the flanking intron sequences and the dystrophin exon are spliced out, resulting in the restoration of an in-frame GFP transcript] were grown in DMEM or RPMI-1640 respectively, and maintained at 37° C. and 10% $CO_2$ in a humidified incubator. $10^4$ or $5 \times 10^4$ cells per well were plated in a 96 or 24 well plate in 100 or 500 µL media with 10% FBS. After 24 hours, cell culture medium was replaced prior to adding polymer/DNA or antisense oligomer (AO) polyplexes formulated with varying ratios of polymer/DNA or AO. PEI 25 k was used as a control for delivery. Cytotoxicity was evaluated using the MTS [3-(4,5-dimethylthiazol-2-yl)-5-(3-carboxymethoxyphenyl)-2-(4-sulfophenyl)-2H-tetrazolium]-based assay by Cell Titer 96®Aqueous One Solution Proliferation Kit (Promega, Madison, Wis.) 24 hours after the treatment with polymers. Transfection efficiencies were determined quantitatively with flow cytometry (BD Biosciences, Sparks, MD) and relative efficiency was also recorded using an Olympus IX 71 inverted microscopy.

Example 10

In Vivo Transfection

Ten mdx mice aged 4 to 6 weeks were used for each experimental group. Plasmid DNA or AO with or without polymer in saline (40 µL) was used for each tibialis anterior (TA) muscle. The muscles were examined 5 days post innoculation of pDNA or 2 weeks post innoculation of AO delivery using an Olympus BX51 fluorescent fluorescent microscope for the expression of GFP. The number of GFP expressing muscle fibers was counted from a minimum of 6 sections spanning at least half length of the muscles. Maximum number of GFP positive fibers in one section for each TA muscle was used for comparison in transfection efficiency. Experimental protocols were approved by the Institutional Animal Care and Use Committee (IACUC), Carolinas Medical Center.

Example 11

Cell Cytotoxicity Assay

Cytotoxicity was evaluated in a C2C12 cell line using the MTS [3-(4,5-dimethylthiazol-2-yl)-5-(3-carboxymethoxyphenyl)-2-(4-sulfophenyl)-2H-tetrazolium]-based assay Cell Titer 96®Aqueous One Solution Proliferation Kit (Promega Corporation, Madison, Mich., USA) 24 hours after the treatment with different doses of polymers.

Cells were seeded in a 96-well tissue culture plate at $10^4$ cells per well in 200 µL medium containing 10% FBS. Cells achieving 70-80% confluence were exposed to polymer at different doses for 24 hours followed by addition of 20 µl of Cell Titer 96 Aqueous One Solution Reagent. After further incubation, 4 hours, the absorbance was measured at 570 nm using a Tecan 500 Plate reader (Tecan US, Inc., Morrisville, N.C., USA) to obtain the metabolic activity of the cell. Viability of untreated cells was taken as 100% and wells without cells were used as blanks. The relative cell viability was calculated by: $(A_{treated} - A_{background}) \times 100 / (A_{control} - A_{background})$. All viability assays were carried out in triplicate.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A compound of Formula I or Formula II:

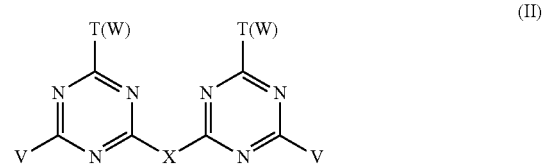

wherein:

T and V are each independently selected from the group consisting of an amphiphilic moiety, a hydrophobic moiety, a hydrophilic moiety, and a therapeutic moiety and W is a cationic moiety selected from the group consisting of a small amine and a polyamine, wherein:
(a) the amphiphilic moiety is selected from the group consisting of a jeffamine, a polysorbate, a poloxamer and a lipoloxamer;
(b) the hydrophilic moiety is selected from the group consisting of an amine-terminated polyethylene glycol ($NH_2$-PEG), polyethylene glycol (PEG) and a polyetheramine;
(c) the hydrophobic moiety is selected from the group selected from the group consisting of an amine-terminated polypropylene glycol ($NH_2$-PPG), and polypropylene glycol; and
(d) the therapeutic agent is selected from the group consisting of oligonucleotides and oligomers capable of complementary binding to DNA or RNA sequences; and X is a linker,
wherein at least one of T, V or W is a polymer and at least one W is always present.

2. The compound of claim 1, wherein the small amine is selected from the group consisting of the following:

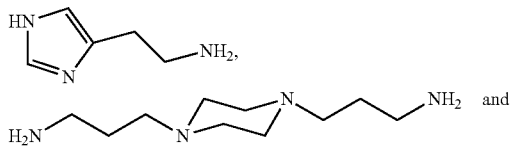

-continued

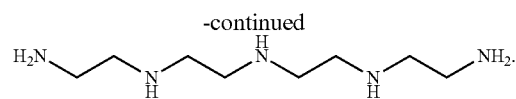

3. The compound of claim 1, wherein the polyamine is selected from the group consisting of a polyethylenimine and a polypropylene imine.

4. The compound of claim 1, wherein X is selected from the group consisting of polyethylene glycol (PEG) and a polyamine.

5. A composition comprising a compound of claim 1 and a pharmaceutically acceptable carrier.

6. The compound of claim 1, wherein the hydrophobic moiety is selected from the group consisting of an amine-terminated polypropylene glycol ($NH_2$-PPG), and polypropylene glycol.

7. The compound of claim 1, wherein one of T or V is a polyetheramine, one of T or V is a therapeutic agent, and W is a polyethyleneimine.

8. The compound of claim 7, wherein the therapeutic agent is a phosphorodiamidate morpholino oligonucleotide (PMO).

9. The compound of claim 1, wherein one of T or V is polypropylene oxide-polyethylene oxide (PPO-PEO) in a mole ratio of 10:31 and the other is a PMO, and W is polyethyleneimine.

10. The compound of claim 7, wherein X is tetraethylenepentamine or 1,6-hexanediamine.

* * * * *

UNITED STATES PATENT AND TRADEMARK OFFICE
CERTIFICATE OF CORRECTION

PATENT NO. : 9,713,623 B2
APPLICATION NO. : 14/674491
DATED : July 25, 2017
INVENTOR(S) : Wang et al.

It is certified that error appears in the above-identified patent and that said Letters Patent is hereby corrected as shown below:

In the Specification

Column 10, Line 3: Please correct "Q (Gin)," to read -- Q (Gln) --
   Lines 39-41: Please correct compound "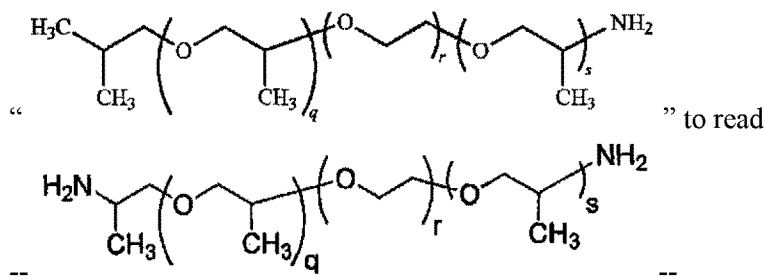" to read --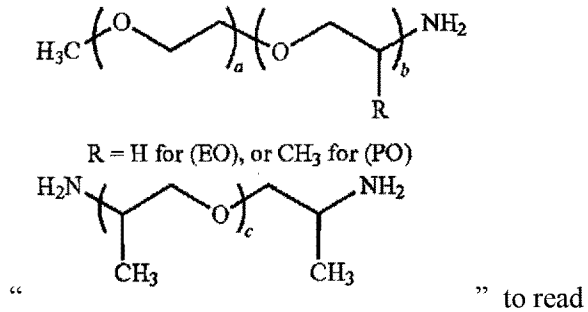--

Column 18, Lines 31-40: Please identify the following structures

"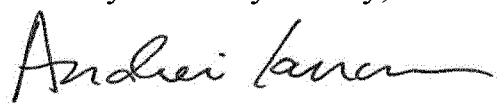" to read

Signed and Sealed this
Thirty-first Day of July, 2018

Andrei Iancu
*Director of the United States Patent and Trademark Office*

CERTIFICATE OF CORRECTION (continued)
U.S. Pat. No. 9,713,623 B2

JEFFAMINE® (M series)

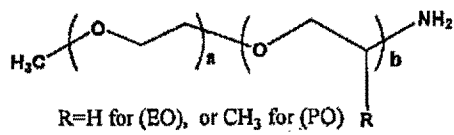

R=H for (EO), or CH$_3$ for (PO)

JEFFAMINE® D Series

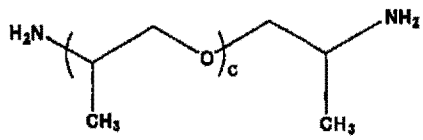

-- --

Lines 42-45, JEFFAMINE® ED Series: Please correct

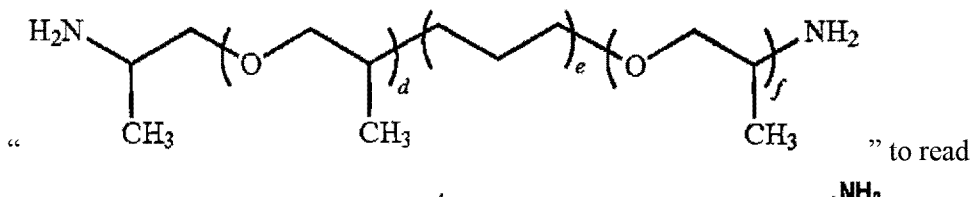

" to read

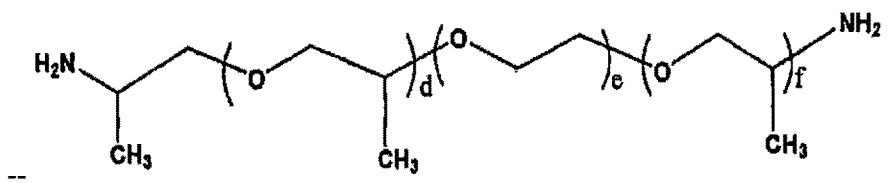

-- --

Column 33, Line 36: Please correct "a-glucosidase inhibitor" to read -- α-glucosidase inhibitor --

Column 40, Example 5, Line 41: Please correct "PEI 1,2 k" to read -- PEI 1.2 k --